United States Patent [19]

Fukuda et al.

[11] Patent Number: 5,599,815
[45] Date of Patent: Feb. 4, 1997

[54] ANTIPSYCHOTIC BENZOISOTHIAZOLYL PIPERAZINE DERIVATIVES

[75] Inventors: Yoshimasa Fukuda; Toshiro Sasaki; Yuuko Nakatani; Yasuyuki Ichimaru; Taiichiro Imanishi, all of Kanagawa, Japan

[73] Assignee: Meiji Seika Kabushiki Kaisha, Tokyo, Japan

[21] Appl. No.: 318,857

[22] PCT Filed: Feb. 3, 1994

[86] PCT No.: PCT/JP94/00159

§ 371 Date: Dec. 20, 1994

§ 102(e) Date: Dec. 20, 1994

[87] PCT Pub. No.: WO94/18197

PCT Pub. Date: Aug. 18, 1994

[30] Foreign Application Priority Data

Feb. 4, 1993 [JP] Japan ..................... 5-017505
Jan. 4, 1994 [WO] WIPO ............. PCT/JP94/00001

[51] Int. Cl.⁶ ............... C07D 417/14; A61K 31/55; A61K 31/50; A61K 31/495
[52] U.S. Cl. ............... 514/254; 514/252; 514/249; 514/258; 514/259; 514/183; 514/217; 514/248; 544/368; 544/363; 544/364; 544/354; 544/282; 544/284; 544/11; 544/52; 544/215; 544/236; 544/235; 544/8; 544/10; 544/47; 544/123; 540/461; 540/592
[58] Field of Search ............... 544/368, 363, 544/364, 354, 282, 284; 514/254, 252, 249, 258, 259

[56] References Cited

U.S. PATENT DOCUMENTS 5,001,130  3/1991  New et al. ................. 544/295

FOREIGN PATENT DOCUMENTS 05320157  12/1993  Japan .

OTHER PUBLICATIONS

Yaso, M. et al. *Chemical Abstract* 120:245,158 (1994).
Asahi Chemical *Derwent World Patent Index* 94–012260 (1994).

*Primary Examiner*—Mukund J. Shah
*Assistant Examiner*—King Lit Wong
*Attorney, Agent, or Firm*—Wenderoth, Lind & Ponack

[57] ABSTRACT

Compounds represented by the formula (I) and pharmacologically acceptable salts thereof:

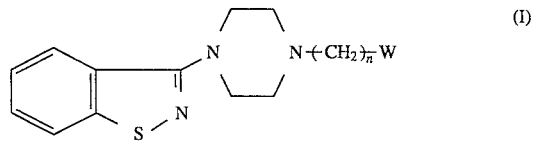

These compounds have little extrapyramidal effect and thus are effective as an anti-psychotic agent having few side effects.

5 Claims, No Drawings

ANTIPSYCHOTIC BENZOISOTHIAZOLYL PIPERAZINE DERIVATIVES

BACKGROUND OF THE INVENTION

This application is a 371 of PCT/JP94/00159 filed Feb. 3, 1994.

1. Field of the Invention

The present invention relates to compounds having an anti-psychotic activity and little extrapyramidal side effect, and to an anti-psychotic agent comprising at least one of the compounds and a pharmacologically acceptable salt thereof as an active ingredient.

2. Related Art

There have hitherto been used chlorpromazine, haloperidol and the like as anti-psychotic agents, which involve central side effects such as extrapyramidal effects, for example parkinsonism. The other side effects thus causing clinically serious problems.

In these years, there have been proposed the compounds of the following formula (I), wherein W represents an imide derivative, such as tiospiron or SM-9018 as the compounds with which the aforementioned problems were to be solved (e.g. in EP 464846, Japanese Patent Laid-Open Publication No. 235865/1990, U.S. Pat. No. 4,968,792, U.S. Pat. No. 4,956,368, WO 9002552, EP 329168, EP 314098, Japanese Patent Laid-Open Publication Nos. 10786/1988 and 83067/1988, and DE 3247530).

There are also known the compounds represented by the following general formula (I) in which W represents —O—R and R represents a phenyl derivative (Japanese Patent Application No. 63263/1990), or an imide or amide derivative (Japanese Patent Application No. 4771/1990). Furthermore, there are similarly known the compounds wherein W represents a group having an amide skeleton such as those described in EP 329168, U.S. Pat. No. 4,933,458 or EP 316723, or W represents an aromatic ring or a heteroaromatic ring which is directly bonded to the main structure without intervening a hetero atom such as described in EP 409435, EP 378255, EP 378255, EP 353821, U.S. Pat. No. 4,831,031 and EP 281309.

Although the above compounds have been reported and that the side effects have successfully been reduced, the ratio of a dose for exhibiting anti-psychotic activity to a dose for exhibiting extrapyramidal side effects such as catalepsy causing action remains relatively small. Thus it has been desired to dissociate sufficiently the difference between the effective dose and the side effect causing dose.

SUMMARY OF THE INVENTION

The present inventors have now found that certain compounds have a strong anti-psychotic activity and little extrapyramidal side effect, and thus accomplished the present invention.

Therefore, an object of the present invention is to provide compounds which have an anti-psychotic activity and little extrapyramidal side effect.

Another object of the present invention is to provide an anti-psychotic agent comprising the above derivative.

The compounds according to the present invention are the compounds represented by the general formula (I)

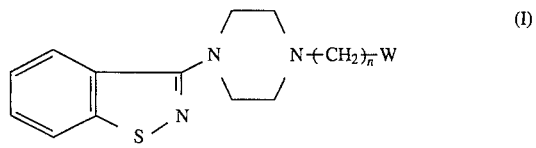

wherein n represents an integer of 2–4, and

W represents any one of the groups represented by the formulae (i)–(xi):

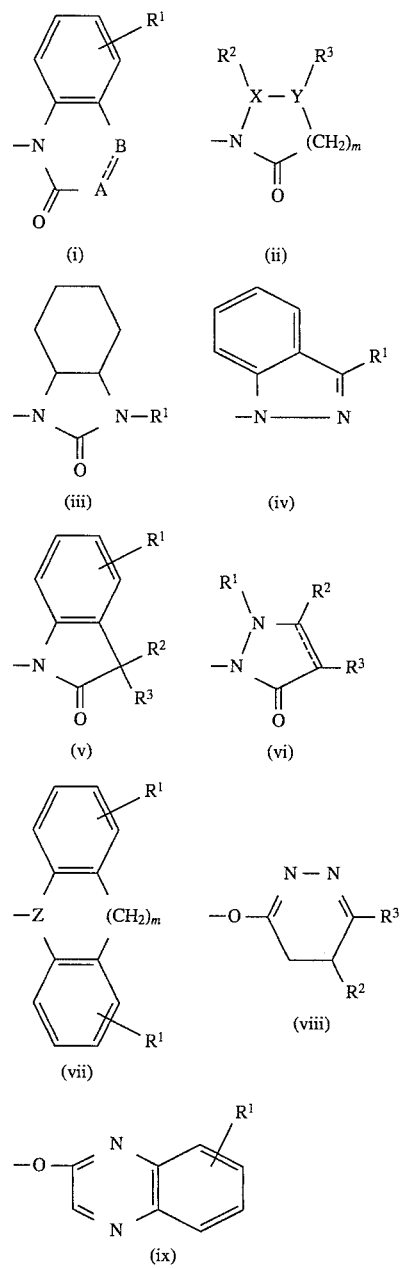

(x)

(xi)

wherein
- m represents an integer of 0–2,
- a solid line accompanying with a dotted line represents a single bond or a double bond,
- A represents $CH_2$, CH, N or NH,
- B represents $CH_2$, CH, N, NH or S, provided that A and B do not simultaneously represent N or NH,
- X represents CH, N, S or a bond,
- Y represents CH or N,
- Z represents a group:

(a)   (b)   (c)

- $R^1$ represents a hydrogen atom, a halogen atom, a lower alkyl group which may be substituted by halogen atoms, a substituted or unsubstituted phenyl group, a hydroxyl group, a nitro group, a lower alkoxy group, an amino group or a cyano group,
- $R^2$ and $R^3$, which may be the same or different, represent a hydrogen atom, a halogen atom, a lower alkyl which may be substituted with halogen, lower alkoxy or amino group or a cyano group, provided that $R^2$ is not present when X represents a bond, or
- $R^2$ and $R^3$ together represent a group $-(CH_2)_p-$, wherein p represents an integer of 3 to 5, to form a substituted or unsubstituted saturated ring or heterocyclic saturated ring, and
- a pharmacologically acceptable salt thereof.

The compounds represented by the general formula (I) have a strong anti-psychotic activity and little extrapyramidal side effect. Therefore, an anti-psychotic agent having safety to humans can be proposed according to the present invention.

DETAILED DESCRIPTION OF THE INVENTION

Compounds of the Formula (I)

The term "lower alkyl" or "lower alkoxy" as a group or a part of a group means herein a straight chain or branched chain alkyl or alkoxy group having 1–6 carbon atoms, preferably 1–4 carbon atoms. The term "halogen atom" means a fluorine atom, a chlorine atom, a bromine atom or an iodine atom.

In the formula (I), W represents groups represented by the formulae (i)–(xi). In these groups, the lower alkyl groups as $R^1$, $R^2$ and $R^3$ which may be substituted with a halogen atom preferably include, for example, trifluoromethyl and monofluoromethyl, and the substituted or unsubstituted phenyl group preferably includes, for example, groups such as lower alkoxy, nitro, cyano or acylamino. Also, in the groups represented by the formulae (ii), (v), (vi) and (vii), $R^2$ and $R^3$ may together represent a group $-(CH_2)_p-$, wherein p represents an integer of 3–5. In other words, $R^2$ and $R^3$ may together form a saturated ring, and particularly form a saturated heterocyclic ring when X or Y represent an N or S atom in the formula (ii).

The compounds according to the present invention preferably include:

- a compound having a group represented by the formula (i) wherein the group $-A \ldots B-$ represents vinylene, $-CH=N-$ or $-CH_2CH_2-$;
- a compound having a group represented by the formula (ii) wherein the group $-X(-R^2)-Y(-R^3)-(CH_2)_m-$ represents $-(CH_2)_4-$, that is to say, $X(-R^2)=Y(-R^3)=CH_2$ and m=2, and a compound having a group represented by the formula (ii) wherein X and Y represent CH and CH or N, respectively, $R^2$ and $R^3$ may together represent a group $-(CH_2)_4-$, and m is 1 or 2;
- a compound having a group represented by the formula (iii) wherein $R^1$ represents a hydrogen atom or a methyl group, and the 6-membered ring involving a dotted line represents a saturated 6-membered ring;
- a compound having a group represented by the formula (iv) wherein $R^1$ represents a chlorine atom,
- a compound having a group represented by the formula (v) wherein $R^1$ represents a hydrogen atom and $R^2$ and $R^3$ may together represent a group $-(CH_2)_4-$, or $R^1$, $R^2$ and $R^3$ represent a hydrogen atom;
- a compound having a group represented by the formula (vi) wherein $R^1$ represents a hydrogen atom or a phenyl group, $R^2$ and $R^3$ represent a hydrogen atom, the bond between carbon atoms to which $R^2$ and $R^3$ are bonded represents a single bond;
- a compound having a group represented by the formula (vii) wherein Z represents either one of the groups (a)–(c), m is 0 or 2, and $R^1$ represents a hydrogen atom, a chlorine atom or a fluorine atom;
- a compound having a group represented by the formula (viii) wherein $R^2$ and $R^3$ may together represent a group $-(CH_2)_4-$;
- a compound having a group represented by the formula (ix) wherein $R^1$ represents a hydrogen atom or a fluorine atom;
- a compound having a group represented by the formula (x) wherein $R^1$ represents a hydrogen atom or a fluorine atom; and
- a compound having a group represented by the formula (xi) wherein $R^1$ represents a hydrogen atom or a fluorine atom, and $R^2$ represents a hydrogen atom or a methyl group.

A particularly preferred group of the compounds according to the present invention is the one represented by the general formula (I) wherein W represents the group of the following formula:

$$-Z \diagup\diagdown (CH_2)_m \qquad (II)$$

wherein m represents an integer of 0 to 2,

Z represents the same meanings as defined in the above formula (vii),

D represents o-phenylene or the following groups

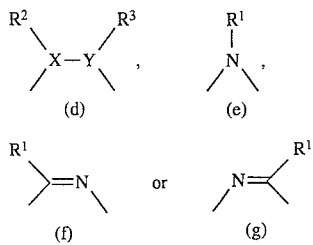

E represents a bond, vinylene, o-phenylene or the following groups

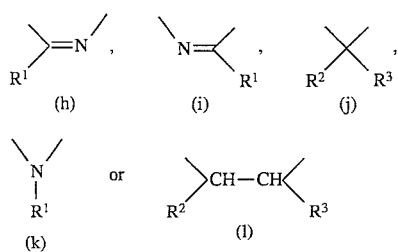

$R^1$, $R^2$, $R^3$, X and Y has the same meanings as defined above, provided that when D represents the group (g) and E represents the group (1), $R^1$ and $R^3$ may together represent —$(CH_2)_q$—, wherein q represents an integer of 3–5, to form a substituted or unsubstituted saturated ring.

Specific examples of the compounds of the present invention further include

1-[4-[4-(1,2-benzisothiazol-3-yl)-1-piperazinyl]butyl]-2(1H)-quinolinone,

9-[4-[4-(1,2-benzisothiazol-3-yl)-1-piperazinyl]butyl]carbazole,

1-[4-[4-(1,2-benzisothiazol-3-yl)-1-piperazinyl]butyl]-2-piperidone,

1-[4-[4-(1,2-benzisothiazol-3-yl)-1-piperazinyl]butyl]spiro[cyclopentane-1,3'-indol-2-one], 1-[4-[4-1,2-benzisothiazol-3-yl)-1-piperazinyl]propyl]-2-(1H)-quinolinone, 5-[4-[4-(1,2-benzisothiazol-3-yl)-1-piperazinyl]butyl]-10,11-dihydro-5H-dibenzo[b,f]azepine, 5-[4-[4-(1,2-benzisothiazol-3-yl)-1-piperazinyl]butyl]-5,6,11,12-tetrahydrodibenz[b,f]azocinn-6-one, 1-[4-[4-(1,2-benzisothiazol-3-yl)-1-piperazinyl]butyl]-3-chloroindazole, 5-[4-[4-(1,2-benzisothiazol-3-yl)-1-piperazinyl]butyl]-6(5H)-phenanthridinone, 6-[4-[4-(1,2-benzisothiazol-3-yl)-1-piperazinyl]butyloxy]phenanthridine, 2-[4-[4-(1,2-benzisothiazol-3-yl)-1-piperazinyl]butyl]phenyl-3-pyrazolidinone, 9-[3-[4-(1,2-benzisothiazol-3-yl)-1-piperazinyl]propyl]carbazole, 1-[4-[4-(1,2-benzisothiazol-3-yl)-1-piperazinyl]butyl]perhydrobenzimidazol-2-one, 1-[3-[4-(1,2-benzisothiazol-3-yl)-1-piperazinyl]propyl]perhydrobenzimidazol-2-one, 1-[2-[4-(1,2-benzisothiazol-3-yl)-1-piperazinyl]ethyl]perhydrobenzimidazol-2-one, 1-[4-[4-(1,2-benzisothiazol-3-yl)-1-piperazinyl]butyl]-3-methylperhydrobenzimidazol-2-one, 1-[3-[4-(1,2-benzisothiazol-3-yl)-1-piperazinyl]propyl]-3-methylperhydrobenzimidazol-2-one, 1-[4-[4-(1,2-benzisothiazol-3-yl)-1-piperazinyl]butyl]perhydroindol-2-one, 3-[4-[4-(1,2-benzisothiazol-3-yl)-1-piperazinyl]butoxy]-4,4a,5,6,7,8-hexahydrocinnoline, 1-[4-[4-(1,2-benzisothiazol-3-yl)-1-piperazinyl]butyl]-1H-quinoxalin-2-one, 2-[4-[4-(1,2-benzisothiazol-3-yl)-1-piperazinyl]butoxy]quinoxaline, 1-[4-[4-(1,2-benzisothiazol-3-yl)-1-piperazinyl]butyl]perhydropyrido[1,2-a]pyrimidin-2-one, 1-[4-[4-(1,2-benzisothiazol-3-yl)-1-piperazinyl]butyl]perhydroquinolin-2-one, 1-[4-[4-(1,2-benzisothiazol-3-yl)-1-piperazinyl]butyl]-1,2,3,4-tetrahydroquinolin-2-one, 4-[1-[4-(1,2-benzisothiazol-3-yl)-1-piperazinyl]butoxy]-2-methylquinazoline, 9-[4-[4-(1,2-benzisothiazol-3-yl)-1-piperazinyl]butyl]-3-chlorocarbazole, 9-[4-[4-1,2-benzisothiazol-3-yl)-1-piperazinyl]butyl]-3,6-dichlorocarbazole, 9-[4-[4-(1,2-benzisothiazol-3-yl)-1-piperazinyl]butyl]-2-chlorocarbazole, 9-[4-[4-(1,2-benzisothiazol-3-yl)-1-piperazinyl]butyl]-4-chlorocarbazole, 9-[4-[4-(1,2-benzisothiazol-3-yl)-1-piperazinyl]butyl]-3-fluorocarbazole, and 9-[4-[4-(1,2-benzisothiazol-3-yl)-1-piperazinyl]butyl]-2-fluorocarbazole, The compounds according to the present invention may be formed into a salt thereof. Such a salt includes pharmacologically acceptable non-toxic salts, for example a hydrogen halide salt such as a hydrochloride salt, an inorganic acid salt such as a sulfuric acid salt, an organic acid salt such as an oxalic acid, citric acid, maleic acid or fumaric acid salt, or an amino acid salt such as a glycine salt. The hydrochloride salt is preferred.

Preparation of the Compounds of the Formula (I)

The compounds according to the present invention may be prepared by the following processes (process A and process B).

According to the first process of the present invention (process A), the compound of the general formula (I) can be prepared by reacting the compound represented by the general formula (III):

$$Hal—(CH_2)_n—W \qquad (III)$$

wherein

W and n represent the same meanings as defined in the formula (I), and Hal represents a halogen atom, and the compound represented by the general formula (IV):

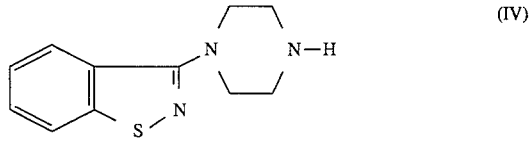

in an inert solvent such as anhydrous acetonitrile, dimethylformamide or tetrahydrofuran in the presence of an acid scavenger and optionally sodium iodide at a reaction temperature of 20°–110° C., preferably 20°–80° C. for 1–24 hours, generally for 2–4 hours.

The scavenger used in the above reaction includes, for example, an alkali metal such as potassium carbonate or sodium hydrogen carbonate, or an organic amine such as triethylamine.

The compounds of the general formula (III) can be prepared according to the following reaction:

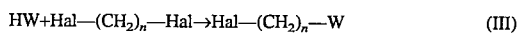

wherein W, Hal and n have the same meanings as defined in general formula (I).

This reaction may be accomplished by performing it in the presence of a base and a small amount of potassium iodide or sodium iodide in an inert solvent such as dimethylformamide or tetrahydrofuran at a reaction temperature of 0°–70° C., preferably 10°–40° C., for 2–24 hours, generally for 5–8 hours.

The base used for the reaction includes potassium hydroxide, sodium hydrogen carbonate, sodium hydride, organic bases such as triethylamine.

In addition, the carbazole substituted with halogen atoms such as fluorine, chlorine or bromine or with a lower alkyl group or a lower alkoxy group which may be substituted with a halogen atom such as fluorine can be synthesized by using an easily available substituted phenylhydrazine in accordance with the methods described in J. Chem. Soc., 1937, 1125; 1953, 3845.

According to the second process of the present invention (process B), the compounds represented by the general formula (I) can be prepared by reacting a compound represented by the general formula:

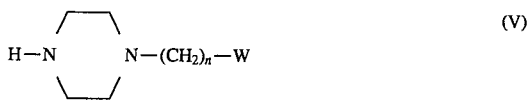

wherein W and n have the same meanings as defined in the general formula (I), with a compound represented by the general formula:

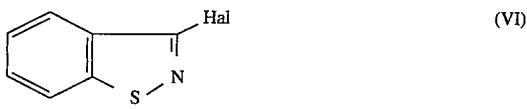

wherein Hal has the same meanings as defined in the general formula (I) in the presence or absence of an inert solvent such as dichloromethane or dimethylformamide in the presence of an acid scavenger at a reaction temperature of 20°–150° C., preferably 80°–120° C. for 2–24 hours, generally for 5–8 hours. As the acid scavenger, there can be used the similar ones used in the process A.

In addition, the compounds represented by the general formula (V) can also be prepared by reacting the compound represented by the formula (III) with piperazine under the same condition as in the process A.

Use of the compound/pharmaceutical composition

The compounds represented by the formula (I) according to the present invention and a pharmacologically acceptable salt thereof have an anti-methanephetamine activity. The compounds according to the present invention and the pharmacologically acceptable salt thereof can therefore be used as an anti-psychotic agent.

The pharmaceutical composition containing the compound according to the present invention as an active ingredient can be administered to humans and the other animals by way of any one of the routes including oral and parenteral administrations such as intravenous injection, intramuscular injection, subcutaneous administration, rectal administration or percutaneous administration. The pharmaceutical composition containing the compound according to the present invention as an active ingredient may therefore be formed into an appropriate preparation corresponding to its route.

Specifically, the oral preparations include a tablet, a capsule, a powder, a granule and a syrup, and the parenteral preparations include injections such as an intravenous injection and an intramuscular injection, a rectal agent, an oleosuppository and an aqueous suppository.

These preparations may be prepared by the usual methods with usually employed components such as an excipient, an disintegrating agent, a binding agent, a lubricating agent, a coloring matter and a diluent.

The excipient includes for example lactose, glucose, corn starch, sorbit and crystalline cellulose; the disintegrating agent includes for example starch, sodium alginate, gelatin powder, calcium carbonate, calcium citrate and dextrin; the binding agent include for example dimethylcellulose, polyvinyl alcohol, polyvinyl ether, methylcellulose, ethylcellulose, gum arabic, gelatin, hydroxypropylcellulose and polyvinylpyrrolidone; and the lubricating agent include for example talc, magnesium stearate, polyethylene glycol and a hydrogenated vegetable oil.

Furthermore, the injections may also be prepared by adding a buffer, a pH regulator or a stabilizing agent, if necessary.

The content of the compound according to the present invention in the pharmaceutical composition depends on the preparations and is generally in the range from 0.5 to 50% by weight, preferably from about 1 to 20% by weight.

The dosage is appropriately determined individually in view of the age, body weight and sex of a patient, diseases and the seriousness of a symptom, and ranges generally from 1 to 1,000 mg, preferably from 5 to 500 mg, which is administered once or in several portions a day.

EXAMPLE

The present invention is now described in detail with reference to the following examples, but it should not be construed to be limited thereto.

EXAMPLE 1

1-[4-[4-(1,2-benzisothiazol-3-yl)-1-piperazinyl]butyl]-2(1H)-quinolinone (a) 1-(4-bromobutyl)-2(1H)-quinolinone 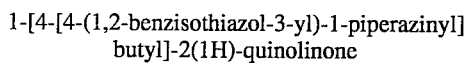

2-hydroxyquinoline (0.29 g, 2.0 mmoles) was dissolved in 4 ml of dimethylformamide, 60% sodium hydride (80 mg, 2.0 mmoles) was added to the solution, and the mixture was stirred at 60° C. for 30 minutes and then cooled to room temperature. 1,4-dibromobutane (2.16 g, 10 mmoles) was further added, and the resulting mixture was stirred at 60° C. for 4 hours. After chloroform was added to the reaction mixture, insolubles were removed by filtration, the filtrate was washed with water, and the solvent was evaporated. The residue thus obtained was purified by chromatography on a silica gel column to give 36 g (yield 64%) of the title compound as an oil.

$^1$H-NMR (CDCl$_3$) δ(ppm): 1.90–2.06 (4H, m, CH$_2$CH$_2$CH$_2$Br), 3.50 (2H, t, J=6.3 Hz, CH$_2$Br), 4.34 (2H, t, J=7.4 Hz, OCH$_2$), 6.69 (1H, d, J=9.2 Hz, H-4), 7.21–7.68 (5H, m, Ar); MW 280.18 (C$_{13}$H$_{14}$NOBr); Mass spectrum EIMS, m/z 281 (M+1)$^+$, 279 (M−1)$^+$.

(b) 1-[4-[4-(1,2-benzisothiazol-3-yl)-1-piperazinyl]butyl]-2(1H)-quinolinone 3-(1-piperazinyl)-1,2-benzisothiazole (0.44 g, 2.0 mmoles), 1-(4-bromobutyl)-2(1H)-quinolinone (0.56 g, 2.0 mmoles) and potassium carbonate (0.33 g, 2.4 mmoles) were suspended in 4 ml of dimethylformamide, and the mixture was stirred at room temperature for 12 hours. Insolubles were removed by filtration, and the solvent was removed under reduced pressure. The residue was purified by chromatography on a silica gel column to give 0.68 g (yield 80%) of the title compound as an oil.

$^1$H-NMR (CDCl$_3$) δ(ppm): 1.70–1.88 (4H, m, CH$_2$CH$_2$CH$_2$Br), 2.53 (2H, t, J=7.2 Hz, NCH$_2$), 2.70 (4H, t, J=4.9 Hz, piperazine CH$_2$), 3.58 (4H, t, J=4.9 Hz, piperazine CH$_2$), 4.36 (2H, t, J=7.8 Hz, OCH$_2$), 6.70 (1H, d, J=9.4 Hz, Ar), 7.81 (1H, d, J=8.0 Hz, Ar), 7.20–7.92 (8H, m, Ar); MW 418.61 (C$_{24}$H$_{24}$N$_4$OS); Mass spectrum EIMS, m/z 418 (M)$^+$.

The oily product (0.68 g, 1.6 mmoles) was taken in 16 ml of dioxane, and 4N dioxane-hydrochloric acid (4 ml, 16 mmoles) was added to the solution to crystallize a white product which was collected by filtration to give the aimed hydrochloride as white powder. Hydrochloride; Mass spectrum EIMS: m/z 418 (M−HCl)$^+$; Mp 223°–225° C.

EXAMPLE 2

9-[4-[4-(1,2-benzisothiazol-3-yl)-1-piperazinyl]butyl]carbazole (a) 9-(4-bromobutyl)carbazole The title compound was synthesized in the same manner as in Example 1 except that 2-hydroxyquinoline was replaced by carbazole.

$^1$H-NMR (CDCl$_3$) δ(ppm): 1.94 (2H, m, CH$_2$), 2.08 (2H, m, CH$_2$), 3.36 (2H, t, J=6.4 Hz, CH$_2$Br), 4.35 (2H, t, J=6.9 Hz, NCH$_2$), 7.25 (2H, m, Ar), 7.40 (2H, m, Ar), 7.47 (2H, m, Ar), 8.10 (2H, dd, J=7.8, 0.6 Hz, Ar); MW 302.33 (C$_{16}$H$_{16}$NBr); Mass spectrum EIMS, m/z 301 (M−1)$^+$, 303 (M+1)$^+$; Mp: 102°–104° C.

(b) 9-[4-[4-(1,2-benzisothiazol-3-yl)-1-piperazinyl]butyl]-carbazole

This compound was prepared by the same manner as in Example 1, except that 1-(4-bromobutyl)-2(1H)-quinolinone was replaced by the compound described in the above paragraph (a).

$^1$H-NMR (CDCl$_3$) δ(ppm): 1.64 (2H, m, CH$_2$), 1.96 (2H, m, CH$_2$), 2.43 (2H, t, J=7.2 Hz, CH$_2$), 2.60 (4H, t, J=4.7 Hz, piperazine CH$_2$), 3.53 (4H, t, J=4.7 Hz, piperazine CH$_2$), 4.36 (2H, t, J=7.2 Hz, CH$_2$N), 7.22 (2H, m, Ar), 7.33 (1H, t, J=7.4 Hz, Ar), 7.45 (6H, m, Ar), 7.86 (1H, d, J=8.0 Hz, Ar), 7.88 (1H, d, J=8.3 Hz, Ar), 8.10 (2H, dd, J=7.8 Hz, Ar); MW 440.66 (C$_{27}$H$_{28}$N$_4$S); Mass spectrum EIMS, m/z 440 (M)$^+$. Hydrochloride: Mass spectrum EIMS: m/z 440 (M−HCl)$^+$; Mp 103°–105° C.

EXAMPLE 3

1-[4-[4-(1,2-benzisothiazol-3-yl)-1-piperazinyl]butyl]-2-piperidone (a) 1-(4-bromobutyl)-2-piperidone 2-piperidone (1.98 g, 20.0 mmoles) was dissolved in 40 ml of dimethylformamide, 60% sodium hydride (840 mg, 21.0 mmoles) was added to the solution, and the mixture was stirred at 80° C. for 1 hour. After cooling the mixture to room temperature, 1,4-dibromobutane (21.6 g, 100 mmoles) was added, and the resulting mixture was stirred at room temperature for 12 hours. After chloroform was added to the reaction mixture, insolubles were removed by filtration, and the filtrate was concentrated under reduced pressure. The residue was dissolved in chloroform and washed with water, and the solvent was evaporated. The residue was purified by chromatography on a silica gel column to give 1.30 g (yield 28%) of the title compound as an oil.

$^1$H-NMR (CDCl$_3$) δ(ppm): 1.68–1.88 (8H, m), 2.37 (2H, t, J=6.2 Hz, piperidone COCH$_2$), 3.28 (2H, t, J=5.7 Hz, piperidone N—CH$_2$), 3.40 (2H, t, J=7.3 Hz, CH$_2$Br), 3.45 (2H, t, J=6.5 Hz, NCH$_2$); MW 234.16 (C$_9$H$_{16}$NOBr); Mass spectrum EIMS, m/z 233 (M−1)$^+$. 235 (M+1)$^+$.

(b) 1-[4-[4-(1,2-benzisothiazol-3-yl)-1-piperazinyl]butyl-2-piperidone

This compound was prepared by the same manner as in Example 1, except that 1-(4-bromobutyl)-2(1H)-quinolinone was replaced by the compound described in the above paragraph (a).

$^1$H-NMR (CDCl$_3$): δ1.51 (4H, m, —CH$_2$—X$_2$), 1.72 (4H, m, —CH$_2$X$_2$), 2.30 (2H, t, J=4.9 Hz, NCH$_2$), 2.38 (2H, t, J=7.2 Hz, COCH$_2$), 2.60 (4H, t, J=4.9 Hz, piperazine CH$_2$), 3.20 (2H, t, J=6.2 Hz, NCH$_2$), 3.32 (2H, t, J=7.1 Hz, NCH$_2$), 3.49 (4H, t, J=5.0 Hz, piperazine CH$_2$), 7.28 (1H, t, J=7.6 Hz, Ar), 7.39 (1H, t, J=7.1 Hz, Ar), 7.73 (1H, d, J=8.2 Hz, Ar), 7.83 (1H, d, J=8.2 Hz, Ar); MW 372.59 (C$_{20}$H$_{28}$N$_4$OS); Mass spectrum EIMS, m/z 372 (M)$^+$. Hydrochloride; mass spectrum EIMS, m/z 372 (M−HCl)$^+$; Mp: 156°–158° C.

EXAMPLE 4

1-[4-[4-(1,2-benzisothiazol-3-yl)-1-piperazinyl]butyl]-spiro[cyclopentan-1,3'-indol-2-one]

(a) 1-(4-bromobutyl)-spiro[cyclopentan-1,3'-indol-2-one]

This compound was prepared in the same manner as in Example 1, except that 2-hydroxyquinoline was replaced by spiro[cyclopentan-1,3'-indol-2-one].

$^1$H-NMR (CDCl$_3$) δ(ppm): 1.84–2.18 (12H, m, CH$_2$), 3.46 (2H, t, J=6.3 Hz, CH$_2$Br), 3.75 (2H, t, J=6.8 Hz, NCH$_2$), 6.85 (1H, d, J=7.8 Hz, Ar), 7.04 (1H, t, J=7.4 Hz, Ar), 7.22 (2H, m, Ar); MW: 322.27 (C$_{10}$H$_{20}$NOBr); Mass spectrum EIMS, m/z 321 (M−1)$^+$, 323 (M+1)$^+$.

(b) 1-[4-[4-(1,2-benzisothiazol-3-yl)-1-piperazinyl]butyl]-spiro[cyclopentan-1,3'-indol-2-one]

This compound was prepared by the same manner as in Example 1, except that 1-(4-bromobutyl)-2(1H)-quinolinone was replaced by the compound described in the above paragraph (a)

¹H-NMR (CDCl₃) δ(ppm): 1.50 (2H, m, CH₂), 1.68 (2H, m, CH₂), 1.75 (2H, m, CH₂), 1.90 (2H, m, CH₂), 2.05 (2H, m, CH₂), 2.40 (2H, t, J=7.4 Hz, piperazine N—CH₂), 2.58 (4H, t, J=4.7 Hz, piperazine CH₂), 3.47 (4H, t, J=4.7 Hz, piperazine CH₂), 3.68 (2H, t, J=7.2 Hz, NCH₂), 6.79 (1H, d, J=7.4 Hz, Ar), 6.95 (1H, t, J=7.6 Hz, Ar), 7.14 (2H, m, Ar), 7.39 (1H, t, J=7.6 Hz, Ar), 7.28 (1H, t, J=7.6 Hz, Ar), 7.73 (1H, d, J=8.2 Hz, Ar), 7.82 (1H, d, J=8.0 Hz, Ar); MW: 460.70 ($C_{27}H_{32}N_4OS$); Mass spectrum EIMS, m/z 460 (M)⁺. Hydrochloride: mass spectrum EIMS, m/z 460 (M–HCl)⁺; Mp: 194°–196° C.

EXAMPLE 5

1-[4-[4-(1,2-benzisothiazol-3-yl)-1-piperazinyl]propyl]-2(1H)-quinolinone (a) 1-(3-bromopropyl)-2(1H)-quinolinone This compound was prepared in the same manner as in Example 1, except that 1,4-dibromobutane was replaced by 1,3-dibromopropane.

¹H-NMR (CDCl₃) δ(ppm): 2.33 (2H, m, CH₂), 3.57 (2H, t, J=6.4 Hz, CH₂Br), 4.46 (2H, t, J=7.6 Hz, OCH₂), 6.70 (1H, d, J=9.5 Hz, quinoline H-3), 7.24 (1H, m, Ar), 7.48 (1H, m, Ar), 7.59 (2H, m, Ar), 7.78 (1H, d, J=9.5 Hz, quinoline H-8); MW: 266.15 ($C_{12}H_{12}NOBr$); Mass spectrum EIMS, m/z 265 (M–1)⁺, 267 (M+1)⁺; Mp: 144°–146° C.

(b) 1-[4-[4-(1,2-benzisothiazol-3-yl)-1-piperazinyl]propyl]-2(1H)-quinolinone

This compound was prepared in the same manner as in Example 1, except that 1-(4-bromobutyl)-2(1H)-quinolinone was replaced by the compound described in the above paragraph (a).

¹H-NMR (CDCl₃) δ(ppm): 1.92 (2H, m, CH₂), 2.52 (2H, t, J=6.8 Hz, CH₂), 2.64 (4H, t, J=4.9 Hz, piperazine CH₂), 3.51 (4H, t, J=4.9 Hz, piperazine CH₂), 4.34 (2H, t, J=7.4 Hz, CH₂O), 6.63 (1H, d, J=9.5 Hz, Ar), 7.14 (1H, m, Ar), 7.29 (1H, t, J=8.2 Hz, Ar), 7.39 (1H, t, J=8.2 Hz, Ar), 7.49 (3H, m, Ar), 7.61 (1H, d, J=9.5 Hz, Ar), 7.74 (1H, d, J=8.2 Hz, Ar), 7.84 (1H, d, J=8.2 Hz, Ar); MW 404.58 ($C_{23}H_{24}N_4OS$); Mass spectrum EIMS, m/z 404 (M)⁺. Hydrochloride: mass spectrum EIMS, m/z 404 (M–HCl)⁺; Mp: 220°–223° C.

EXAMPLE 6

5-[4-[4-(1,2-benzisothiazol-3-yl)-1-piperazinyl]butyl]-10,11-dihydro-5H-dibenz[b,f]azepine (a) 5-(4-bromobutyl)-10,11-dihydro-5H-dibenz[b,f]azepine This compound was prepared in the same manner as in Example 1, except that 2-hydroxyquinoline was replaced by 10,11-dihydro-5H-dibenz[b,f]azepine.

¹H NMR (CDCl₃): δ1.73 (2H, m, CH₂), 1.89 (2H, m, CH₂), 1.89 (2H, m, CH₂), 3.16 (4H, s, —C₆H₄—CH₂X₂), 3.33 (2H, t, J=6. Hz, BrCH₂), 3.77 (2H, t, J=6.7 Hz, NCH₂), 6.92 (2H, m, Ar), 7.10 (6H, m, Ar); MW: 330.29 ($C_{18}H_{20}NBr$); Mass spectrum EIMS, m/z 331 (M+1)⁺, 329 (M–1)⁺.

(b) 5-[4-[4-(1,2-benzisothiazol-3-yl)-1-piperazinyl]butyl]-10,11-dihydro-5H-dibenz[b,f]azepine This compound was prepared in the same manner as in Example 1, except that 1-(4-bromobutyl)-2(1H)-quinolinone was replaced by the compound described in the above paragraph (a).

¹H-NMR (CDCl₃): δ1.60 (4H, m, —CH₂—X₂), 2.38 (2H, t, J=7.19 Hz, NCH₂), 2.58 (4H, s, —C₆H₄CH₂CH₂), 3.51 (4H, t, J=4.6 Hz, piperazine CH₂), 3.78 (2H, t, J=6.4 Hz, NCH₂), 6.91 (2H, t, J=6.8 Hz, Ar), 7.10 (6H, m, Ar), 7.33 (1H, t, J=7.7 Hz, Ar), 7.55 (1H, t, J=8.1 Hz, Ar), 7.80 (1H, d, J=8.0 Hz, Ar), 7.88 (1H, d, J=7.8 Hz, Ar); MW: 468.72 ($C_{29}H_{32}N_4S$); Mass spectrum EIMS, m/z 468 (M)⁺. Hydrochloride: mass spectrum EIMS m/z 468 (M–HCl)⁺; Mp: 205°–207° C.

EXAMPLE 7

5-[4-[4-(1,2-benzisothiazol-3-yl)-1-piperazinyl]butyl]-5,6,11,12-tetrahydrodibenz[b,f]azocin-6-one This compound was prepared in the same manner as in Example 1, except that 2-hydroxyquinoline is replaced by 5,6,11,12-tetrahydrodibenz[b,f]azocinn-6-one.

¹H-NMR (CDCl₃): δ1.83 (4H, m, CH₂), 2.90 (2H, m, —C₆H₄CH₂—), 3.44 (2H, m, —C₆H₄CH₂—), 3.63 (2H, m, CH₂Br), 4.16 (2H, m, NCH₂), 6.89 (1H, m, Ar), 7.05 (6H, m, Ar), 7.17 (1H, m, Ar); MW: 358.13 ($C_{19}H_{20}NOBr$); Mass spectrum EIMS, m/z 359 (M+1)⁺, 357 (M–1)⁺.

(b) 5-[4-[4-(1,2-benzisothiazol-3-yl)-1-piperazinyl]butyl]-5,6,11,12-tetrahydrodibenz[b,f]azocin-6-one This compound was prepared in the same manner as in Example 1, except that 1-(4-bromobutyl)-2(1H)-quinolinone was replaced by the compound described in the above paragraph (a).

¹H-NMR (CDCl₃): δ1.60 (4H, m, CH₂), 2.47 (2H, t, NCH₂), 2.66 (4H, t, piperazine CH₂), 2.90 (2H, m, —C₆H₄—CH₂), 3.30 (1H, m, —C₆H₄—CH₂), 3.42 (1H, m, —C₆H₄—CH₂), 3.55 (4H, t, piperazine CH₂), 3.60 (1H, m, NCH₂), 4.20 (1H, m, NCH₂), 6.90 (1H, m, NCH₂), 7.17 (1H, m, Ar), 7.35 (1H, t, J=7.6 Hz, Ar), 7.46 (1H, t, J=8.0 Hz, Ar), 7.80 (1H, d, J=8.0 Hz, Ar), 7.90 (1H, d, J=8.0 Hz, Ar); MW: 496.73 ($C_{30}H_{32}N_4OS$); Mass spectrum EIMS, m/z 496 (M)⁺. Hydrochloride: mass spectrum EIMS m/z 496 (M–HCl)⁺; Mp: 122°–124° C.

EXAMPLE 8

1-[4-[4-(1,2-benzisothiazol-3-yl)-1-piperazinyl]butyl]-3-chloroindazole (a) 1-(4-bromobutyl)-3-chloroindazole This compound was prepared in the same manner as in Example 1, except that 2-hydroxyquinoline was replaced by 3-chloroindazole.

¹H-NMR (CDCl₃): δ1.86 (2H, m, CH₂), 2.08 (2H, m, CH₂), 3.38 (2H, t, J=6.6 Hz, CH₂Br), 4.36 (2H, t, J=6.8 Hz, NCH₂), 7.20 (1H, m, Ar), 7.43 (2H, m, Ar), 7.66 (1H, m, Ar); MW: 287.60 ($C_{11}H_{12}N_2ClBr$); Mass spectrum EIMS, m/z 288 (M+1)⁺, 286 (M–1)⁺ Mp: 260° C.

(b) 1-[4-[4-(1,2-benzisothiazol-3-yl)-1-piperazinyl]butyl]-3-chloroindazole

This compound was synthesized in the same manner as in Example 1, except that 1-(4-bromobutyl)-2(1H)-quinolinone was replaced by the compound described in the above paragraph (a).

$^1$H-NMR (CDCl$_3$): δ1.56 (2H, m, CH$_2$), 2.00 (2H, m, CH$_2$), 2.44 (2H, t, J=7.4 Hz, piperazine —NCH$_2$), 2.62 (4H, t, J=4.9 Hz, piperazine CH$_2$), 3.53 (4H, t, J=4.9 Hz, piperazine CH$_2$), 4.37 (2H, t, J=7.0 Hz, —NCH$_2$), 7.19 (1H, t, J=8.0 Hz, Ar), 7.40 (4H, m, Ar), 7.67 (1H, d, J=8.2 Hz, Ar), 7.79 (1H, d, J=8.2 Hz, Ar), 7.88 (1H, d, J=8.2 Hz, Ar); MW: 426.03 (C$_{22}$H$_{24}$N$_5$SCl); Mass spectrum EIMS, m/z 426 (M)$^+$. Hydrochloride: mass spectrum EIMS m/z 425 (M–1–HCl)$^+$; Mp: 217°–219° C.

EXAMPLE 9

5-[4-[4-(1,2-benzisothiazol-3-yl)-1-piperazinyl]butyl]-6(5H)-phenanthrizinone

(a) 5-(4-bromobutyl)-6 (5H)-phenanthrizinone

This compound was synthesized in the same manner as in Example 1, except that 2-hydroxyquinoline was replaced by 6-hydroxyphenanthrizine.

$^1$H-NMR (CDCl$_3$): δ2.10 (4H, m, CH$_2$CH$_2$), 3.51 (2H, t, J=6.5 Hz, CH$_2$Br), 4.63 (2H, t, J=6.1 Hz, NCH$_2$), 7.43 (1H, t, J=7.6 Hz, Ar), 7.58 (2H, m, Ar), 7.75 (1H, t, J=7.6 Hz, Ar), 7.82 (1H, t, J=8.6 Hz, Ar), 8.30 (1H, d, J=7.8 Hz, Ar), 8.37 (1H, d, J=7.8 Hz, Ar), 8.45 (1H, d, J=8.2 Hz, Ar); MW: 330.24 (C$_{17}$H$_{16}$NOBr); Mass spectrum EIMS, m/z 329 (M–1)$^+$, 331 (M+1)$^+$ Mp: 65°–67° C.

(b) 5-[4-[4-(1,2-benzisothiazol-3-yl)-1-piperazinyl]butyl]-6(5H)-phenanthrizinone This compound was synthesized in the same manner as in Example 1, except that 1-(4-bromobutyl)-2(1H)-quinolinone was replaced by the compound described in the above paragraph (a).

$^1$H-NMR (CDCl$_3$): δ1.80 (2H, m, CH$_2$), 1.90 (2H, m, CH$_2$), 2.55 (2H, t, J=7.2 Hz, piperazine N—CH$_2$), 2.72 (4H, t, J=4.7 Hz, piperazine CH$_2$), 3.59 (4H, t, J=4.9 Hz, piperazine CH$_2$), 4.46 (2H, t, J=7.8 Hz, NCH$_2$), 7.35 (2H, m, Ar), 7.46 (1H, t, J=7.8 Hz, Ar), 7.55 (2H, m, Ar), 7.59 (1H, t, J=8.0 Hz, Ar), 7.76 (1H, dr, J=7.4, 1.6 Hz, Ar), 7.81 (1H, d, J=8.2 Hz, Ar), 7.91 (1H, t, J=8.2 Hz, Ar), 8.30 (1H, t, J=8.4 Hz, Ar), 8.56 (1H, dd, J=7.8, 1.2 Hz, Ar); MW: 468.67 (C$_{28}$H$_{28}$N$_4$OS); Mass spectrum EIMS, m/z 468 (M)$^+$. Hydrochloride: mass spectrum EIMS m/z 468 (M–HCl)$^+$; Mp: 163°–165° C.

EXAMPLE 10

6-[4-[4-(1,2-benzisothiazol-3-yl)-1-piperazinyl]butyloxy]phenanthrizine

(a) 5-(4-bromobutyloxy)phenanthrizine

This compound was prepared together with the compound described in Example 9 (a) and isolated and purified by chromatography on a silica gel column.

$^1$H-NMR (CDCl$_3$): δ2.03 (4H, m, CH$_2$CH$_2$), 3.51 (2H, t, J=6.5 Hz, CH$_2$Br), 4.45 (2H, t, J=7.2 Hz, OCH$_2$), 7.33 (1H, dr, J=7.6, 1.2 Hz, Ar), 7.43 (1H, d, J=8.2 Hz, Ar), 7.58 (2H, m, Ar), 7.77 (1H, m, Ar), 8.30 (2H, m, Ar), 8.53 (1H, dd, J=7.8, 0.8 Hz, Ar); MW: 330.24 (C$_{17}$H$_{16}$NOBr); Mass spectrum EIMS, m/z 329 (M–1)$^+$, 331 (M+1)$^+$ Mp: 54°–56° C.

(b) 6-[4-[4-(1,2-benzisothiazol-3-yl)-1-piperazinyl]butyloxy]phenanthrizine This compound was synthesized in the same manner as in Example 1, except that 1-(4-bromobutyl)-2(1H)-quinolinone was replaced by the compound described in the above paragraph (a).

$^1$H-NMR (CDCl$_3$): δ1.87 (2H, m, CH$_2$), 2.03 (2H, m, CH$_2$), 2.59 (2H, t, J=7.6 Hz, piperazine N—CH$_2$), 2.73 (4H, t, J=4.7 Hz, piperazine CH$_2$), 3.59 (4H, t, J=4.7 Hz, piperazine CH$_2$), 4.69 (2H, t, J=6.4 Hz, OCH$_2$), 7.35 (1H, t, J=7.0 Hz, Ar), 7.46 (2H, m, Ar), 7.61 (2H, m, Ar), 7.80 (2H, m, Ar), 7.87 (2H, m, Ar), 8.38 (1H, d, J=8.2 Hz, Ar), 8.42 (1H, t, J=8.2 Hz, Ar), 8.51 (1H, d, J=8.2 Hz, Ar); MW: 468.67 (C$_{28}$H$_{28}$N$_4$OS); Mass spectrum EIMS, m/z 468 (M)$^+$. Hydrochloride: mass spectrum EIMS m/z 468 (M–HCl)$^+$; Mp: 233°–235° C.

EXAMPLE 11

2-[4-[4-(1,2-benzisothiazol-3-yl)-1-piperazinyl]butyl]-1-phenyl-3-pyrazolidinone

(a) 2-(4-bromobutyl)-1-phenyl-3-pyrazolidinone

This compound was prepared in the same manner as in Example 1, except that 2-hydroxyquinoline was replaced by 1-phenyl-3-pyrazolidinone.

$^1$H-NMR (CDCl$_3$): δ1.78 (2H, m, CH$_2$), 1.88 (2H, m, CH$_2$), 2.52 (2H, t, J=7.5 Hz, CH$_2$CO), 3.43 (2H, t, J=6.5 Hz, CH$_2$Br), 3.46 (2H, t, J=6.7 Hz, CH$_2$), 3.80 (2H, t, J=7.6 Hz, CH$_2$), 6.96 (2H, m, Ar), 7.11 (1H, m, Ar), 7.33 (2H, m, Ar); MW: 297.22 (C$_{13}$H$_{17}$N$_2$OBr); Mass spectrum EIMS, m/z 298 (M+1)$^+$, 296 (M–1)$^+$ Mp: 187°–189° C.

(b) 2-[4-[4-(1,2-benzisothiazol-3-yl)-1-piperazinyl]butyl]-1-phenyl-3-pyrazolidinone This compound was synthesized in the same manner as in Example 1, except that 1-(4-bromobutyl)-2(1H)-quinolinone was replaced by the compound described in the above paragraph (a).

$^1$H-NMR (CDCl$_3$): δ1.66 (2H, m, CH$_2$), 1.78 (2H, m, CH$_2$), 2.52 (2H, t, J=7.4 Hz, CH$_2$CO), 2.65 (4H, t, J=5.0 Hz, piperazine CH$_2$), 3.47 (2H, t, J=7.1 Hz, CH$_2$N—N(CO)), 3.54 (4H, t, J=5.0 Hz, piperazine CH$_2$), 3.80 (2H, t, J=7.4 Hz, CH$_2$), 6.97 (2H, m, Ar), 7.10 (1H, t, J=7.4 Hz, Ar), 7.34 (1H, m, Ar), 7.46 (1H, m, Ar), 7.80 (1H, d, J=8.0 Hz, Ar), 7.90 (1H, d, J=8.0 Hz, Ar); MW: 435.65 (C$_{24}$H$_{29}$N$_5$OS); Mass spectrum EIMS, m/z 435 (M)$^+$. Hydrochloride: mass spectrum EIMS m/z 435 (M–HCl)$^+$; Mp: 111°–113° C.

EXAMPLE 12

9-[3-[4-(1,2-benzisothiazol-3-yl)-1-piperazinyl]propyl]carbazole

The compound was prepared in the same manner as in Example 1, except that 9-(4-bromobutyl)carbazole is replaced by 9-(3-bromopropyl)carbazole.

$^1$H-NMR (CDCl$_3$) δ(ppm): 2.09 (2H, tt, J=6.7, 6.7 Hz, CH$_2$), 2.37 (2H, t, J=6.7 Hz, piperazine N—CH$_2$), 2.61 (4H, t, J=5.0 Hz, piperazine), 3.58 (4H, t, J=5.0 Hz, piperazine ), 4.44 (2H, t, J=6.7 Hz, N—CH$_2$), 7.23 (2H, m, Ar), 7.34 (1H, m, Ar), 7.43–7.52 (5H, m, Ar), 7.80 (1H, d, J=8.3 Hz, Ar), 7.88 (1H, d, J=8.1 Hz, Ar), 8.10 (2H, d, J=7.8 Hz, Ar); MW: 426.63 ($C_{26}H_{28}N_4S$) Mass spectrum EIMS, m/z 426 (M)$^+$. Hydrochloride: mass spectrum EIMS, m/z 426 (M–HCl)$^+$; Mp: 204°–206° C.

EXAMPLE 13

1-[4-[4-(1,2-benzisothiazol-3-yl)-1-piperazinyl]butyl]perhydrobenzimidazol-2-one (a) 3-benzoyl-1-(4-bromobutyl)perhydrobenzimidazol-2-one To a solution of 3-benzoylperhydrobenzimidazol-2-one (2.7 9, 10.0 mmoles) in 50 ml of dimethylformamide was added 60% sodium hydride (400 mg, 10.0 mmoles), and the mixture was stirred at 60° C. for 30 minutes. To this mixture having been cooled to room temperature was further added 1,4-dibromobutane (10.8 g, 50.0 mmoles), and the resulting mixture was stirred at 60° C. for 4 hours. After chloroform was added to the reaction, insolubles were removed by filtration, the filtrate was washed with water, and the solvent was evaporated. The residue thus obtained was purified by chromatography on a silica gel column to give 1.5 g of the title compound as an oil.

$^1$H-NMR (CDCl$_3$) δ(ppm): 1.40–1.90 (11H, m), 2.27 (1H, m), 3.10 (1H, m, NCH$_2$), 3.44 (3H, m, BrCH$_2$, NCH$_2$), 4.40 (1H, m, NCH), 7.40 (2H, m, Ar), 7.48 (1H, m, Ar), 7.55 (1H, m, Ar); MW: 379.33 ($C_{18}H_{23}N_2O_2Br$); Mass spectrum EIMS, m/z 378 (M–1)$^+$, 380 (M+1)$^+$.

(b) 3-benzoyl-1-[4-[4-(1,2-benzisothiazol-3-yl)-1-piperazinyl]butyl]perhydrobenzimidazol-2-one A suspension of 3-(1-piperazinyl)-1,2-benzisothiazole (0.44 g, 2.0 mmoles), 3-benzoyl-1-(4-bromobutyl)perhydrobenzimidazol-2-one (0.76 g, 2.0 mmoles) and potassium carbonate (0.33 g, 2.4 mmoles) in 4 ml of dimethylformamide was stirred at 60° C. for 2 hours. Insolubles were removed by filtration, and the solvent was evaporated under reduced pressure. The residue was dissolved in chloroform and washed with water, and the solvent was evaporated. The residue was purified by chromatography on a silica gel column to give 1.0 g of the title compound as an oil.

$^1$H-NMR (CDCl$_3$) δ(ppm): 1.30–1.70 (8H, m), 1.80 (2H, m), 1.90 (2H, m), 2.25 (2H, m), 2.44 (2H, t, J=6.9 Hz, piperazinde N—CH$_2$), 2.65 (4H, t, J=5.1Hz, piperazine), 3.08 (1H, m, NCH), 3.45 (1H, m, NCH), 3.55 (4H, t, J=5.1 Hz, piperazine), 3.76 (1H, m, NCH$_2$), 4.40 (1H, m, NCH$_2$), 7.33–7.41 (3H, m, Ar), 7.44–7.50 (2H, m, Ar), 7.55–7.58 (2H, m, Ar), 7.81 (1H, d, J=8.2 Hz, Ar), 7.90 (1H, m, J=8.2 Hz, Ar); MW: 517.76 ($C_{29}H_{35}N_5O_2S$); Mass spectrum EIMS, m/z 517 (M)$^+$.

(c) 1-[4-[4-(1,2-benzisothiazol-3-yl)-1-piperazinyl]butyl]perhydrobenzimidazol-2-one The compound (1.0 g, 1.9 mmoles) obtained in the above described paragraph (b) was dissolved in the mixed solution of 3 ml of dioxane and 3 ml of concentrated aqueous ammonia, and the resulting solution was heated in a sealed tube at 120° C. for 24 hours. The reaction was concentrated under reduced pressure, and the residue was then purified by chromatography on a silica gel column to give 0.56 g of the title compound.

$^1$H-NMR (CDCl$_3$) δ(ppm): 1.30–1.75 (12H, m), 2.45 (2H, t, J=6.9 Hz, piperazine NCH$_2$), 3.00 (1H, m, NHCH), 3.44 (1H, m, NCH), 3.57 (6H, m, piperazine, NCH$_2$), 4.26 (1H, br s, NH), 7.35 (1H, t, J=7.6 Hz, Ar), 7.49 (1H, m, Ar), 7.81 (1H, m, Ar), 7.90 (1H, m, Ar); MW: 413.65 ($C_{22}H_{31}N_5OS$); Mass spectrum EIMS, m/z 413 (M)$^+$.

To the solution of the oil in dioxane was added 4N dioxane-hydrochloric acid, and the resulting precipitates were collected by filtration to give the aimed hydrochloride as a white powder. Hydrochloride: mass spectrum EIMS, m/z 413 (M–HCl)$^+$; Mp: 111°–113° C.

EXAMPLE 14

1-[3-[4-(1,2-benzisothiazol-3-yl)-1-piperazinyl]propyl]perhydrobenzimidazol-2-one This compound was prepared in the same manner as in Example 13, except that 3-benzoyl-1-(4-bromobutyl)perhydrobenzimidazol-2-one is replaced by 3-benzoyl-1-(3-bromopropyl)perhydro-benzimidazol-2-one.

$^1$H-NMR (CDCl$_3$) δ(ppm): 1.30–1.40 (2H, m ), 1.48 (1H, m ), 1.50–1.62 (2H, m), 1.66–1.72 (5H, m), 2.52 (2H, m, piperazine NCH$_2$), 2.73 (4H, br s, piperazine), 3.04 (1H, m, NCH$_2$), 3.46 (1H, m, NCH$_2$), 3.55–3.62 (6H, m, piperazine, NCH, NHCH), 4.47 (1H, br s, NH), 7.35 (1H, t, J=8.3 Hz, Ar), 7.47 (1H, t, J=8.0 Hz, Ar), 7.81 (1H, d, J=8.0 Hz, Ar), 7.90 (1H, d, J=8.3 Hz, Ar); MW: 399.62 ($C_{21}H_{29}N_5OS$); Mass spectrum EIMS, m/z 399 (M)$^+$. Hydrochloride: mass spectrum EIMS, m/z 399 (M–HCl)$^+$; Mp: 232°–235° C.

EXAMPLE 15

1-[2-[4-(1,2-benzisothiazol-3-yl)-1-piperazinyl]ethyl]perhydrobenzimidazol-2-one This compound was prepared in the same manner as in Example 13, except that 3-benzoyl-1-(4-bromobutyl)perhydrobenzimidazol-2-one was replaced by 3-benzoyl-1-(2-bromoethyl)perhydro-benzimidazol-2-one.

$^1$H-NMR (CDCl$_3$) δ(ppm): 1.30–1.40 (2H, m), 1.45–1.65 (3H, m), 1.65–1.80 (3H, m), 2.53–2.65 (2H, m, piperazine N—CH$_2$), 2.73 (4H, t, J=5.0 Hz, piperazine), 3.11 (1H, m, NHCH$_2$), 3.55 (5H, m, NCH$_2$, piperazine), 3.55–3.73 (2H, m, NCHX$_2$), 4.36 (1H, br s, NH), 7.36 (1H, t, J =8.3 Hz, Ar), 7.47 (1H, t, J=8.0 Hz, Ar), 7.80 (1H, d, J=8.0 Hz, Ar), 7.90 (1H, d, J=8.3 Hz, Ar); MW: 385.59 ($C_{20}H_{27}N_5OS$); Mass spectrum EIMS, m/z 385 (M)$^+$. Hydrochloride: mass spectrum EIMS, m/z 385 (M–HCl)$^+$; Mp: 171°–173° C.

EXAMPLE 16

1-[4-[4-(1,2-benzisothiazol-3-yl)-1-piperazinyl]butyl]-3-methylperhydrobenzimidazol-2-one (a) 1-(4-bromobutyl)-3-methylperhydrobenzimidazol-2-one This compound was prepared in the same manner as in Example 1, except that 2-hydroxy-quinoline is replaced by 3-methylperhydrobenzimidazol-2-one.

$^1$H-NMR (CDCl$_3$) δ(ppm): 1.25–1.80 (10H, m), 1.90 (2H, m), 2.72 (3H, s, CH$_2$), 2.98 (1H, m, NCH), 3.29 (1H, m, NCH), 3.37–3.47 (4H, m, BrCH$_2$, NCH$_2$); MW: 289.25 ($C_{12}H_{21}N_2OBr$); Mass spectrum EIMS, m/z 288 (M–1)$^+$, 290 (M+1)$^+$.

(b) 1-[4-[4-(1,2-benzisothiazol-3-yl)-1-piperazinyl]butyl]-3-methylperhydrobenzimidaz-2-one This compound was prepared in the same manner as in Example 1, except that 1-(4-bromobutyl)-2(1H)-quinolinone is replaced by 1-(4-bromobutyl)-3-methylperhydrobenzimidazol-2-one.

$^1$H-NMR (CDCl$_3$) δ(ppm): 1.25–1.80 (12H, m), 2.46 (2H, t, J=6.6 Hz, piperazine NCH$_2$), 2.67 (4H, t, J=4.7 Hz, piperazine), 2.72 (3H, s, CH$_2$), 2.95 (1H, m, NCH), 3.28 (1H, m, NCH), 3.44 (2H, m, NCH$_2$) 3.57 (4H, t, J=4.7 Hz, piperazine), 7.36 (1H, t, J=7.0 Hz, Ar), 7.47 (1H, t, J =7.0 Hz, Ar), 7.80 (1H, d, J=8.2 Hz, Ar), 7.90 (1H, d, J=8.2 Hz, Ar); MW: 427.68 (C$_{23}$H$_{33}$N$_5$OS); Mass spectrum EIMS, m/z 427 (M)$^+$. Hydrochloride: mass spectrum EIMS, m/z 427 (M–HCl)$^+$; Mp: 212°–214° C.

EXAMPLE 17

1-[3-[4-(1,2-benzisothiazol-3-yl)-1-piperazinyl]propyl]-3-methylperhydrobenzimidazol-2-one This compound was prepared in the same manner as in Example 1, except that 1-(4-bromobutyl)-2(1H)-quinolinone is replaced by 1-(3-bromopropyl)-3-methylperhydrobenzimidazol-2-one.

$^1$H-NMR (CDCl$_3$) δ(ppm): 1.25–1.60 (5H, m), 1.65–1.82 (5H, m ), 2.50 (2H, m, piperazine NCH$_2$), 2.69 (4H, t, J=4.7 Hz, piperazine ), 2.72 (3H, s, CH$_3$), 3.01 (1H, m, NCH$_2$), 3.30 (1H, ddd, J=6.4, 5.3, 5.3 Hz, NCH), 3.33–3.40 (2H, m, NCH$_2$, NCH) 7.35 (1H, t, J=8.2 Hz, Ar), 7.46 (1H, t, J=8.0 Hz, Ar), 7.80 (1H, d, J=8.0 Hz, Ar), 7.90 (1H, d, J=8.2 Hz, Ar); MW: 413.65 (C$_{22}$H$_{31}$N$_5$OS); Mass spectrum EIMS, m/z 413 (M)$^+$. Hydrochloride: mass spectrum EIMS, m/z 413 (M–HCl)$^+$; Mp: 99°–101° C.

EXAMPLE 18

1-[4-[4-(1,2-benzisothiazol-3-yl)-1-piperazinyl]butyl]perhydroindol-2-one

(a) 1-(4-bromobutyl)perhydroindol-2-one

This compound was prepared in the same manner as in Example 1, except that 2-hydroxyquinoline was replaced by perhydroindol-2-one.

$^1$H-NMR (CDCl$_3$) δ(ppm): 1.30–1.85 (12H, m), 2.15 (1H, m), 2.33 (2H, m, COCH$_2$), 2.95 (1H, m ), 3.45 (2H, t, J=6.5 Hz, BrCH$_2$), 3.55 (1H, m, NCH$_2$), 3.65 (1H, m, NCH$_2$); MW: 274.23 (C$_{12}$H$_{20}$NOBr); Mass spectrum EIMS, m/z 273 (M–1)$^+$, 275 (M+1)$^+$.

(b) 1-[4-[4-(1,2-benzisothiazol-3-yl)-1-piperazinyl]butyl]perhydroindol-2-one This compound was prepared in the same manner as in Example 1, except that 1-(4-bromobutyl)-2(1H)-quinolinone was replaced by 1-(4-bromobutyl)perhydroindol-2-one.

$^1$H-NMR (CDCl$_3$) δ(ppm): 1.30–1.80 (12H, m), 2.15 (1H, m, CH), 2.31 (2H, m, COCH$_2$), 2.45 (2H, t, J=6.9 Hz, piperazine NCH$_2$), 2.67 (4H, t, J=4.9 Hz, piperazine), 2.92 (1H, m, NCH), 3.56 (5H, m, piperazine, NCH$_2$), 3.66 (1H, m, NCH$_2$), 7.35 (1H, t, J=8.2 Hz, Ar), 7.46 (1H, t, J=8.2 Hz, Ar), 7.80 (1H, d, J=8.2 Hz, Ar), 7.90 (1H, d, J=8.2 Hz, Ar); MW: 412.66 (C$_{23}$H$_{32}$N$_4$OS); Mass spectrum EIMS, m/z 412 (M)$^+$. Hydrochloride: mass spectrum EIMS, m/z 412 (M–HCl)$^+$; Mp: 195°–198° C.

EXAMPLE 19

3-[4-[4-(1,2-benzisothiazol-3-yl)piperazinyl]butoxy]-4,4a,5,6,7,8-hexahydrocinnoline

(a) 3-(4-bromobutoxy)-4,4a,5,6,7,8-hexahydrocinnoline

This compound was prepared in the same manner as in Example 1, except that 2-hydroxyquinoline is replaced by 4,4a,5,6,7,8hexahydrocinnoline.

$^1$H-NMR (CDCl$_3$) δ(ppm): 1.20–1.31 (1H, m), 1.25–1.43 (2H, m), 1.85–1.90 (5H, m), 1.93–2.02 (1H, m), 2.05–2.20 (3H, m), 2.46–2.65 (3H, m), 3.44 (2H, t, J=6.6 Hz, BrCH$_2$), 3.74 (2H, t, J=6.8 Hz, OCH$_2$); MW: 287.23 (C$_{12}$H$_{19}$N$_2$OBr); Mass spectrum EIMS, m/z 286 (M–1)$^+$, 288 (M+1)$^+$.

(b) 3-[4-[4-(1,2-benzisothiazol-3-yl)piperazinyl]butoxy]-4,4a,5,6,7,8-hexahydrocinnoline This compound was prepared in the same manner as in Example 1, except that 1-(4-bromobutyl)-2(1H)-quinolinone is replaced by 3-(4-bromobutoxy )-4,4a,5,6,7,8-hexahydrocinnoline.

$^1$H-NMR (CDCl$_3$) δ(ppm): 1.20–1.30 (1H, m), 1.35–1.40 (2H, m), 1.51–1.60 (2H, m), 1.65–1.76 (3H, m), 1.80–2.00 (2H, m), 2.05–2.20 (3H, m), 2.47 (2H, t, J=7.6 Hz, piperazine NCH$_2$), 2.49–2.64 (2H, m ), 2.67 (4H, t, J=5.1 Hz, piperazine ), 3.55 (4H, t, J=5.1 Hz, piperazine ), 3.73 (2H, t, J=6.9 Hz, OCH$_2$), 7.35 (1H, t, J=8.2 Hz, Ar), 7.46 (1H, t, J=8.2 Hz, Ar), 7.80 (1H, d, J=8.2 Hz, Ar), 7.90 (1H, d, J=8.2 Hz, Ar); MW: 425.66 (C$_{23}$H$_{31}$N$_5$OS); Mass spectrum EIMS, m/z 425 (M)$^+$. Hydrochloride: mass spectrum EIMS, m/z 425 (M–HCl)$^+$; Mp: 71°–73° C.

EXAMPLE 20

1-[4-[4-(1,2-benzisothiazol-3-yl)-1-piperazinyl]butyl]-1H-quinoxaline-2-one

(a) 1-(4-bromobutyl)-1H-quinoxaline-2-one

This compound was prepared in the same manner as in Example 1, except that 2-hydroxyquinoline was replaced by 2-hydroxyquinoxaline.

$^1$H-NMR (CDCl$_3$) δ(ppm): 1.85–1.95 (4H, m, CH$_2$CH$_2$), 3.45 (2H, t, J=6.1 Hz, BrCH$_2$), 4.25 (2H, t, J=7.3 Hz, NCH$_2$), 7.32 (2H, m, Ar), 7.57 (1H, m, Ar), 7.86 (1H, d, J=8.4 Hz, Ar), 8.25 (1H, s, Ar); MW: 281.17 (C$_{12}$H$_{13}$N$_2$OBr); Mass spectrum EIMS, m/z 280 (M–1)$^+$, 282 (M+1)$^+$; Mp: 74°–76° C.

(b) 1-[4-[4-(1,2-benzisothiazol-3-yl)-1-piperazinyl]butyl]-1H -quinoxalin-2-one This compound was prepared in the same manner as in Example 1, except that 1-(4-bromobutyl)-2(1H)-quinolinone was replaced by 1-(4-bromobutyl)-1H-quinoxalin-2-one.

$^1$H-NMR (CDCl$_3$) δ(ppm): 1.76–1.83 (2H, m, CH$_2$), 1.92–1.99 (2H, m, CH$_2$), 2.56 (2H, t, J=7.4 Hz, piperazine NCH$_2$), 2.73 (4H, t, J=4.9 Hz, piperazine ), 3.60 (4H, t, J=4.9 Hz, piperazine), 4.55 (2H, t, J=6.5 Hz, NCH$_2$), 7.37 (1H, m, Ar), 7.48 (1H, m, Ar), 7.57 (1H, m, Ar), 7.69 (1H, m, Ar), 7.84 (2H, m, Ar), 7.92 (1H, d, J=8.2 Hz), 8.03 (1H, d, J=8.2 Hz, Ar), 8.48 (1H, s, Ar); MW: 419.6 ($C_{23}H_{25}N_5OS$); Mass spectrum EIMS, m/z 419 (M)$^+$. Hydrochloride: mass spectrum EIMS, m/z 419 (M–HCl); Mp: 128°–130° C.

EXAMPLE 21

2-[4-[4-(1,2-benzisothiazol-3-yl)-1-piperazinyl]butoxy]quinoxaline (a) 2-(4-bromobutoxy) quinoxaline This compound was prepared in the same manner as in Example 1, except that 2-hydroxyquinoline was replaced by 2-hydroxyquinoxaline.

$^1$H-NMR (CDCl$_3$) δ(ppm): 2.01–2.11 (4H, m, CH$_2$CH$_2$), 3.52 (2H, t, J=6.5 Hz, BrCH$_2$), 4.52 (2H, t, J=6.1 Hz, OCH$_2$), 7.56 (1H, m, Ar), 7.67 (1H, m, Ar), 7.82 (1H, m, Ar), 8.01 (1H, d, J=8.0 Hz, Ar), 8.46 (1H, s, Ar); MW: 281.17 ($C_{12}H_{13}N_2OBr$); Mass spectrum EIMS, m/z 282 (M+1)$^+$, 280 (M–1)$^+$; Mp: 87°–88° C.

(b) 2-[4-[4-(1,2-benzisothiazol-3-yl)-1-piperazinyl]butoxy]quinoxaline

This compound was prepared in the same manner as in Example 1, except that 1-(4-bromobutyl)-2(1H)-quinolinone was replaced by 1-(4-bromobutyl)-1H-quinoxalin-2-one.

$^1$H-NMR (CDCl$_3$) δ(ppm): 1.76–1.88 (4H, m, CH$_2$CH$_2$), 2.53 (2H, t, J=7.2 Hz, piperazine, NCH$_2$), 2.70 (4H, t, J=4.9 Hz, piperazine ), 3.58 (4H, t, J=4.9 Hz, piperazine), 4.31 (2H, t, J=7.7 Hz, OCH$_2$), 7.36 (2H, m, Ar), 7.47 (2H, m, Ar), 7.60 (1H, m, Ar), 7.81 (1H, d, J=8.2 Hz, Ar), 7.90 (2H, m, Ar), 8.31 (1H, s, Ar); MW: 419.6 ($C_{23}H_{25}N_5OS$); Mass spectrum EIMS, m/z 419 (M)$^+$. Hydrochloride: mass spectrum EIMS, m/z 419 (M–HCl); Mp: 110°–113° C.

EXAMPLE 22

1-[4-[4-(1,2-benzisothiazol-3-yl)-1-piperazinyl]butyl]perhydropyrido[1,2-a]pyrimidin-2-one (a) 1-(4-bromobutyl)perhydropyrido[1,2-a]pyrimidin-2-one This compound was prepared in the same manner as in Example 1, except that 2-hydroxyquinoline was replaced by perhydropyrido[1,2-a]pyrimidin-2-one.

$^1$H-NMR (CDCl$_3$) δ(ppm): 1.39 (1H, m), 1.47 (1H, m), 1.77 (1H, m), 1.87 (2H, m), 2.08 (1H, m), 2.35 (2H, m), 2.55 (1H, m), 2.68 (1H, m), 2.88 (1H, m), 2.95 (1H, m), 3.32 (1H, m), 3.44 (2H, m, BrCH$_2$), 3.52 (2H, m); MW: 289 ($C_{12}H_{21}N_2OBr$); Mass spectrum EIMS, m/z 290 (M)$^+$;

(b) 1-[4-[4-(1,2-benzisothiazol-3-yl)-1-piperazinyl]butyl]perhydropyrido[1,2-a]pyrimidin-2-one This compound was prepared in the same manner as in Example 1, except that 1-(4-bromobutyl)-2(1H)-quinolinone was replaced by 1-(4-bromobutyl)perhydropyrido[1,2-a]pyrimidin-2-one.

$^1$H-NMR (CDCl$_3$) δ(ppm): 1.30–1.75 (8H, m), 1.80–1.88 (1H, m), 2.05–2.12 (1H, m), 2.30–2.41 (2H, m), 2.45 (2H, t, J=7.2 Hz, piperazine NCH$_2$), 2.52–2.60 (1H, m), 2.63–2.73 (5H, m, piperazine), 2.84–2.90 (1H, m), 2.91–2.97 (1H, m), 3.27–3.34 (1H, m), 3.50–3.60 (6H, m), 7.35 (1H, ddd, J=8.2, 6.9, 1.0 Hz, Ar), 7.46 (1H, ddd, J=8.2, 6.8, 1.0 Hz, Ar), 7.80 (1H, d, J=8.2 Hz, Ar), 7.90 (1H, d, J=8.2 Hz, Ar); MW: 427.68 ($C_{23}H_{33}N_5OS$); Mass spectrum EIMS, m/z 427 (M)$^+$. Hydrochloride: mass spectrum EIMS, m/z 427 (M–HCl); Mp: 110°–113° C.

EXAMPLE 23

1-[4-[4-(1,2-benzisothiazol-3-yl)-1-piperazinyl]butyl]perhydroquinoline-2-one (a) 1-(4-bromobutyl)perhydroquinolin-2-one This compound was prepared in the same manner as in Example 1, except that 2-hydroxyquinoline was replaced by perhydroquinolin-2-one.

$^1$H-NMR (CDCl$_3$) δ(ppm): 1.21 (1H, m), 1.32 (2H, m), 1.48 (2H, m), 1.68 (1H, m), 1.74 (4H, m), 1.86 (3H, m), 2.07 (2H, m), 2.41 (2H, m), 2.87 (1H, m), 3.21 (1H, m), 3.44 (2H, t, J=6.5 Hz, BrCH$_2$), 3.80 (1H, m ); MW: 288.22 ($C_{13}H_{22}NOBr$); Mass spectrum EIMS, m/z 289 (M+1)$^+$.

(b) 1-[4-[4-(1,2-benzisothiazol-3-yl)-1-piperazinyl]butyl]perhydroquinolin-2-one This compound was prepared in the same manner as in Example 1, except that 1-(4-bromobutyl)-2(1H)-quinolinone was replaced by 1-(4-bromobutyl)perhydroquinolin-2-one.

$^1$H-NMR (CDCl$_3$) δ(ppm): 1.18–1.80 (12H, m), 1.89–1.94 (1H, m), 2.00–2.10 (2H, m), 2.35–2.50 (4H, m, COCH$_2$, piperazine NCH$_2$), 2.77 (4H, t, J=4.7 Hz, piperazine), 2.87 (1H, m, NCH$_2$), 3.22 (1H, m, NCH), 3.57 (4H, t, J=4.7 Hz, piperazine ), 3.81 (1H, m, NCH$_2$), 7.35 (1H, ddd, J=8.2, 7.0, 1.2 Hz, Ar), 7.46 (1H, ddd, J=8.2, 7.0, 1.2 Hz, Ar), 7.80 (1H, d, J=8.2 Hz, Ar), 7.90 (1H, d, J=8.2 Hz, Ar); MW: 426.69 ($C_{24}H_{34}N_4OS$); Mass spectrum EIMS, m/z 426 (M)$^+$; Mp: 100°–102° C. Hydrochloride: mass spectrum SIMS, m/z 427 (M–HCl)$^+$; Mp: 200°–230° C.

EXAMPLE 24

1-[4-[4-(1,2-benzisothiazol-3-yl)-1-piperazinyl]butyl]-1,2,3,4-tetrahydroquinolin-2-one (a) 1-(4-bromobutyl)-1,2,3,4-tetrahydroquinolin-2-one This compound was prepared in the same manner as in Example 1, except that 2-hydroxy-quinoline was replaced by 1,2,3,4-tetrahydroquinoline.

$^1$H-NMR (CDCl$_3$) δ(ppm): 1.82 (2H, m, CH$_2$), 1.94 (2H, m, CH$_2$), 2.67 (2H, m, COCH$_2$), 2.98 (2H, m, PhCH$_2$), 3.45 (2H, t, J=6.7 Hz, BrCH$_2$), 3.98 (2H, t, J=7.2 Hz, NCH$_2$), 7.01 (2H, m), 7.17 (1H, m), 7.26 (2H, m); MW: 282.17 ($C_{13}H_{16}NOBr$); Mass spectrum EIMS, m/z 281 (M–1)$^+$, 283 (M+1)$^+$.

(b) 1-[4-[4-(1,2-benzisothiazol-3-yl)-1-piperazinyl]butyl]-1,2,3,4-tetrahydroquinolin-2-one This compound was prepared in the same manner as in Example 1, except that 1-(4-bromobutyl)-2(1H)-quinolinone was replaced by 1-(4-bromobutyl)-1,2,3,4-tetrahydroquinolin-2-one.

$^1$H-NMR (CDCl$_3$) δ(ppm): 1.62–1.69 (2H, m, CH$_2$), 1.71–1.77 (2H, m, CH$_2$), 2.49 (2H, t, J=7.2 Hz, piperazine NCH$_2$), 2.63–2.70 (6H, m, COCH$_2$, piperazine), 2.89 (2H, m, PhCH$_2$), 3.57 (4H, t, J=4.9 Hz, piperazine), 3.99 (2H, t, J=7.2 Hz, NCH$_2$), 7.02 (1H, t, J=7.2 Hz, Ar), 7.08 (1H, d, J=8.2 Hz, Ar), 7.16 (1H, d, J=7.2 Hz, Ar), 7.25 (1H, m, Ar), 7.36 (1H, m, Ar), 7.47 (1H, m, Ar), 7.81 (1H, dd, J=8.2, 0.8 Hz, Ar), 7.91 (1H, dd, J=8.2, 0.8 Hz, Ar); MW: 420.63 (C$_{24}$H$_{28}$N$_4$OS); Mass spectrum EIMS, m/z 420 (M)$^+$. Hydrochloride: mass spectrum EIMS, m/z 420 (M–HCl)$^+$; Mp: 210°–212° C.

EXAMPLE 25

4-[1-[4-(1,2-benzisothiazol-3-yl)-1-piperazinyl]butoxy]-2-methylquinazoline (a) 4-(4-bromobutoxy)-2-methylquinazoline This compound was prepared in the same manner as in Example 1, except that 2-hydroxy-quinoline was replaced by 4-hydroxy-2-methylquinazoline.

$^1$H-NMR (CDCl$_3$) δ(ppm): 2.05–2.23 (4H, m, CH$_2$CH$_2$), 2.53 (2H, t, J=6.4 Hz, OCH$_2$), 3.60 (2H, t, J=6.0 Hz, BrCH$_2$), 6.48 (1H, m), 7.76 (1H, m), 7.83 (1H, m), 8.10 (1H, m); MW: 295.18 (C$_{13}$H$_{15}$N$_2$OBr); Mass spectrum EIMS, m/z 296 (M+1)$^+$. Mp: >240° C.

(b) 4-[1-[4-(1,2-benzisothiazol-3-yl)-1-piperazinyl]butoxy]-2-methylquinazoline

This compound was prepared in the same manner as in Example 1, except that 1-(4-bromobutyl)-2(1H)-quinolinone was replaced by 4-(4-bromobutoxy)-2-methylquinazoline.

$^1$H-NMR (CDCl$_3$) δ(ppm): 1.76–1.83 (2H, m, CH$_2$), 1.93–2.00 (2H, m, CH$_2$), 2.55 (2H, t, J=7.4 Hz, piperazine NCH$_2$), 2.71 (4H, t, J=4.9 Hz, piperazine), 2.72 (3H, s, CH$_3$), 3.58 (4H, t, J=4.9 Hz, piperazine), 4.61 (2H, t, J =6.4 Hz, OCH$_2$), 7.35 (1H, ddd, J=8.2, 6.9, 1.0 Hz, Ar), 7.44–7.50 (2H, m, Ar), 7.75–7.84 (3H, m, Ar), 7.90 (1H, d, J=8.2 Hz, Ar), 8.13 (1H, dd, J=8.2, 0.8 Hz, Ar); MW: 433.63 (C$_{24}$H$_{27}$N$_5$OS); Mass spectrum EIMS, m/z 433 (M)$^+$. Hydrochloride: mass spectrum EIMS, m/z 433 (M–HCl)$^+$; Mp: 182°–185° C.

EXAMPLE 26

9-[4-[4-(1,2-benzisothiazol-3-yl)-1-piperazinyl]butyl]-3-chlorocarbazole (a) 9-(4-bromobutyl)-3-chlorocarbazole This compound was prepared in the same manner as in Example 1, except that 2-hydroxyquinoline was replaced by 3-chlorocarbazole.

$^1$H-NMR (CDCl$_3$) δ(ppm): 1.83–1.92 (2H, m, CH$_2$), 2.00–2.07 (2H, m, CH$_2$), 3.36 (2H, t, J=6.4 Hz, BrCH$_2$), 4.31 (2H, t, J=6.9 Hz, ArNCH$_2$), 7.24 (1H, ddd, J=8.2, 6.9, 1.1 Hz, Ar), 7.37 (2H, d, J=7.5 Hz, Ar), 7.40 (1H, dd, J =8.7, 2.1 Hz, Ar), 7.48 (1H, ddd, J=8.2, 6.9, 1.1 Hz, Ar), 8.02–8.04 (2H, m, Ar); MW: 336.67 (C$_{16}$H$_{15}$NBrCl); Mass spectrum EIMS, m/z 335 (M)$^+$.

(b) 9-[4-[4-(1,2-benzisothiazol-3-yl)-1-piperazinyl]butyl]-3-chlorocarbazole

This compound was prepared in the same manner as in Example 1, except that 1-(4-bromobutyl)-2(1H)-quinolinone was replaced by 9-(4-bromobutyl)-3-chlorocarbazole.

$^1$H-NMR (CDCl$_3$) δ(ppm): 1.55–1.65 (2H, m, CH$_2$), 1.96–1.99 (2H, m, CH$_2$), 2.42 (2H, t, J=7.4 Hz, NCH$_2$), 2.59 (4H, t, J=4.9 Hz, piperazine ), 3.53 (4H, t, J=4.9 Hz, piperazine ), 4.30 (2H, t, J=7.2 Hz, ArNCH$_2$), 7.42–7.48 (4H, m, Ar), 7.80 (1H, d, J=8.2 Hz, Ar), 7.87 (1H, d, J =8.2 Hz, Ar), 7.98 (1H, d, J=2.0 Hz, Ar); MW: 475.1 (C$_{27}$H$_{27}$N$_4$SCl); Mass spectrum EIMS, m/z 474 (M)$^+$. Hydrochloride: mass spectrum EIMS, m/z 474 (M–HCl)$^+$; Mp: 211°–214° C.

EXAMPLE 27

9-[4-[4-(1,2-benzisothiazol-3-yl)-1-piperazinyl]butyl]-3,6-dichlorocarbazole (a) 9-(4-bromobutyl)-3,6-dichlorocarbazole This compound was prepared in the same manner as in Example 1, except that 2-hydroxyquinoline was replaced by 3,6-dichlorocarbazole.

$^1$H-NMR (CDCl$_3$) δ(ppm): 1.84–1.90 (2H, m, CH$_2$), 1.98–2.05 (2H, m, CH$_2$), 3.37 (2H, t, J=6.4 Hz, BrCH$_2$), 4.29 (2H, t, J=7.1 Hz, ArNCH$_2$), 7.29 (2H, d, J=8.6 Hz, Ar), 7.42 (2H, dd, J=8.6, 1.9 Hz, Ar), 7.98 (2H, d, J=1.9 Hz, Ar); MW: 371.11 (C$_{16}$H$_{14}$NBrCl$_2$); Mass spectrum EIMS, m/z 369 (M)$^+$; Mp: 115°–117° C.

(b) 9-[4-[4-(1,2-benzisothiazol-3-yl)-1-piperazinyl]butyl]-3,6-dichlorocarbazole This compound was prepared in the same manner as in Example 1, except that 1-(4-bromobutyl)-2(1H)-quinolinone is replaced by 9-(4-bromobutyl)-3,6-dichlorocarbazole.

$^1$H-NMR (CDCl$_3$) δ(ppm): 1.55–1.65 (2H, m, CH$_2$), 1.89–1.97 (2H, m, CH$_2$), 2.43 (2H, t, J=7.3 Hz, NCH$_2$), 2.59 (4H, t, J=4.9 Hz, piperazine), 3.53 (4H, t, J=4.9 Hz, piperazine), 4.33 (2H, t, J=7.2 Hz, ArNCH$_2$), 7.32–7.36 (2H, m, Ar), 7.41–7.50 (4H, m, Ar), 7.79 (1H, d, J=8.0 Hz, Ar), 7.87 (1H, d, J=8.0 Hz, Ar), 8.03–8.05 (2H, m, Ar); MW: 509.54 (C$_{27}$H$_{26}$N$_4$SCl$_2$); Mass spectrum EIMS, m/z 508 (M)$^+$. Hydrochloride: mass spectrum EIMS, m/z 508 (M–HCl)$^+$; Mp: 190°–193° C.

EXAMPLE 28

9-[4-[4-(1,2-benzisothiazol-3-yl)-1-piperazinyl]butyl]-2-chlorocarbazole (a) 9-(4-bromobutyl)-2-chlorocarbazole This compound was prepared in the same manner as in Example 1, except that 2-hydroxy-quinoline was replaced by 2-chlorocarbazole.

$^1$H-NMR (CDCl$_3$) δ(ppm): 1.87–1.94 (2H, m, CH$_2$), 2.00–2.07 (2H, m, CH$_2$), 3.38 (2H, t, J=6.4 Hz, BrCH$_2$), 4.29 (2H, t, J=6.9 Hz, ArNCH$_2$), 7.18–7.40 (1H, m, Ar), 7.22–7.26 (1H, m, Ar), 7.36–7.40 (2H, m, Ar), 7.47 (2H, ddd, J=8.2, 7.1, 1.2 Hz, Ar), 7.97 (1H, d, J=8.2 Hz, Ar) 8.04 (1H, d, J=8.2 Hz, Ar); MW: 336.67 (C$_{16}$H$_{15}$NBrCl); Mass spectrum EIMS, m/z 335 (M)$^+$;

(b) 9-[4-[4-(1,2-benzisothiazol-3-yl)-1-piperazinyl]butyl]-2-chlorocarbazole

The compound was prepared in the same manner as in Example 1, except that 1-(4-bromobutyl)-2(1H)-quinolinone is replaced by 9-(4-bromobutyl)-2-chlorocarbazole.

¹H-NMR (CDCl₃) δ(ppm): 1.56–1.64 (2H, m, CH$_2$), 1.90–1.96 (2H, m, CH$_2$), 2.42 (2H, t, J=7.3 Hz, NCH$_2$), 2.59 (4H, t, J=4.9 Hz, piperazine), 3.53 (4H, t, J=4.9 Hz, piperazine), 4.27 (2H, t, J=7.3 Hz, ArNCH$_2$), 7.17 (1H, dd, J=8.2, 1.8 Hz, Ar), 7.20–7.25 (1H, m, Ar), 7.32 (1H, dd, J=8.2, 0.9 Hz, Ar), 7.37–7.48 (4H, m, Ar), 7.78 (1H, d, J=8.0 Hz, Ar), 7.87 (1H, d, J=8.0 Hz, Ar), 7.96 (1H, d, J=8.2 Hz, Ar), 8.03 (1H, d, J=7.7 Hz, Ar); MW: 475.1 (C$_{27}$H$_{27}$N$_4$SCl); Mass spectrum EIMS, m/z 474 (M)$^+$. Hydrochloride: mass spectrum EIMS, m/z 474 (M–HCl)$^+$; Mp: 211°–214° C.

EXAMPLE 29

9-[4-[4-(1,2-benzisothiazol-3-yl)-1-piperazinyl]butyl]-4-chlorocarbazole (a) 9-(4-bromobutyl)-4-chlorocarbazole This compound was prepared in the same manner as in Example 1, except that 2-hydroxy-quinoline was replaced by 4-chlorocarbazole.

¹H-NMR (CDCl₃) δ(ppm): 1.86–1.94 (2H, m, CH$_2$), 2.00–2.09 (2H, m, CH$_2$), 3.37 (2H, t, J=6.5 Hz, BrCH$_2$), 4.34 (2H, t, J=6.9 Hz, ArNCH$_2$), 7.20–7.22 (1H, m, Ar), 7.28–7.31 (2H, m, Ar), 7.35–7.40 (2H, m, Ar), 7.49 (1H, m, Ar), 8.62 (1H, d, J=8.0 Hz, Ar); MW: 336.67 (C$_{16}$H$_{15}$NBrCl); Mass spectrum EIMS, m/z 335 (M)$^+$; Mp: 106°–108° C.

(b) 9-[4-[4-(1,2-benzisothiazol-3-yl)-1-piperazinyl]butyl]-4-chlorocarbazole

This compound was prepared in the same manner as in Example 1, except that 1-(4-bromobutyl)-2(1H)-quinolinone is replaced by 9-(4-bromobutyl)-4-chlorocarbazole.

¹H-NMR (CDCl₃) δ(ppm): 1.58–1.66 (2H, m, CH$_2$), 1.90–1.98 (2H, m, CH$_2$), 2.43 (2H, t, J=7.4 Hz, NCH$_2$), 2.60 (4H, t, J=4.9 Hz, piperazine), 3.53 (4H, t, J=4.9 Hz, piperazine), 4.35 (2H, t, J=7.2 Hz, ArNCH$_2$), 7.20 (1H, dd, J=7.1, 1.4 Hz, Ar), 7.28 (1H, ddd, J=8.2, 7.1, 0.9 Hz, Ar), 7.31–7.37 (3H, m, Ar), 7.43–7.42 (2H, m, Ar), 7.52 (1H, ddd, J=8.2, 7.1, 0.9 Hz, Ar), 7.79 (1H, dd, J =8.2, 7.1, 0.9 Hz, Ar), 7.87 (1H, d, J=8.2 Hz, Ar), 8.62 (1H, dd, J=8.0, 0.9 Hz, Ar); MW: 475.1 (C$_{27}$H$_{27}$N$_4$SCl); Mass spectrum EIMS, m/z 474 (M)$^+$. Hydrochloride: mass spectrum EIMS, m/z 474 (M–HCl)$^+$; Mp: 158°–160° C.

EXAMPLE 30

9-[4-[4-(1,2-benzisothiazol-3-yl)-1-piperadinyl]butyl]-3-fluorocarbazole (a) 9-(4-bromobutyl)-3-fluorocarbazole This compound was prepared in the same manner as in Example 1, except that 2-hydroxy-quinoline was replaced by 3-fluorocarbazole.

¹H-NMR (CDCl₃) δ(ppm): 1.85–1.93 (2H, m, CH$_2$), 2.00–2.09 (2H, m, CH$_2$), 3.37 (2H, t, J=6.4 Hz, BrCH$_2$), 4.32 (2H, t, J=6.9 Hz, NCH$_2$), 7.17–7.24 (3H, m, Ar), 7.29 (1H, dd, J=8.6, 4.2 Hz, Ar), 7.38 (1H, d, J=8.2 Hz, Ar), 7.48 (1H, ddd, J=8.2, 7.1, 0.2 Hz, Ar), 7.74 (1H, dd, J=8.2 Hz, Ar), 8.03 (1H, d, J=8.0 Hz, Ar); MW: 320.22 (C$_{16}$H$_{15}$NBrF); Mass spectrum EIMS, m/z 319 (M)$^+$; Mp: 54°–56° C.

(b) 9-[4-[4-(1,2-benzisothiazol-3-yl)-1-piperazinyl]butyl]-3-fluorocarbazole

This compound was prepared in the same manner as in Example 1, except that 1-(4-bromobutyl)-2(1H)-quinolinone is replaced by 9-(4-bromobutyl)-3-fluorocarbazole.

¹H-NMR (CDCl₃) δ(ppm): 1.58–1.65 (2H, m, CH$_2$), 1.90–1.98 (2H, m, CH$_2$), 2.43 (2H, t, J=7.4 Hz, NCH$_2$), 2.60 (4H, t, J=4.9 Hz, piperazine), 3.53 (4H, t, J=4.9 Hz, piperazine), 4.34 (2H, t, J=7.2 Hz, ArNCH$_2$), 7.17–7.23 (2H, m, Ar), 7.32–7.36 (2H, m, Ar), 7.41 (1H, d, J=8.1 Hz, Ar), 7.45 (1H, ddd, J=8.2, 7.1, 1.1 Hz, Ar), 7.48 (1H, ddd, J=8.2, 7.1, 1.1 Hz, Ar), 7.74 (1H, dd, J=8.9, 2.5 Hz, Ar), 7.77 (1H, d, J=8.1 Hz, Ar), 7.87 (1H, d, J =8.3 Hz, Ar), 8.04 (1H, d, J=7.9 Hz, Ar); MW: 458.65 (C$_{27}$H$_{27}$N$_4$SF); Mass spectrum EIMS, m/z 458 (M)$^+$. Hydrochloride: mass spectrum EIMS, m/z 458 (M–HCl)$^+$; Mp: 212°–215° C.

EXAMPLE 31

9-[4-[4-(1,2-benzisothiazol-3-yl)-1-piperadinyl]butyl]-2-fluorocarbazole (a) 9-(4-bromobutyl)-2-fluorocarbazole This compound was prepared in the same manner as in Example 1, except that 2-hydroxy-quinoline was replaced by 2-fluorocarbazole.

¹H-NMR (CDCl₃) δ(ppm): 1.88–1.95 (2H, m, CH$_2$), 2.01–2.08 (2H, m, CH$_2$), 3.37 (2H, t, J=6.4 Hz, BrCH$_2$), 4.28 (2H, t, J=6.9 Hz, ArNCH$_2$), 6.95 (1H, ddd, J=9.2, 8.7, 2.3 Hz, Ar), 7.04 (1H, dd, J=9.8, 2.3 Hz, Ar), 7.24 (1H, dd, J=9.8, 2.3 Hz, Ar), 7.24 (1H, dd, J=7.7, 0.8 Hz, Ar), 7.37 (1H, d, J=8.2 Hz, Ar), 7.44 (1H, ddd, J=8.2, 7.2 1.0 Hz, Ar), 7.99 (1H, dd, J=8.7, 5.6 Hz, Ar), 8.02 (1H, d, J=7.7 Hz, Ar); MW: 320.22 (C$_{16}$H$_{15}$NBrF); Mass spectrum EIMS, m/z 319 (M)$^+$; Mp: 60°–61° C.

(b) 9-[4-[4-(1,2-benzisothiazol-3-yl)-1-piperazinyl]butyl]-2-fluorocarbazole

This compound was prepared in the same manner as in Example 1, except that 1-(4-bromobutyl)-2(1H)-quinolinone is replaced by 9-(4-bromobutyl)-2-fluorocarbazole.

¹H-NMR (CDCl₃) δ(ppm): 1.58–1.66 (2H, m, CH$_2$), 1.90–1.98 (2H, m, CH$_2$), 2.44 (2H, t, J=7.4 Hz, NCH$_2$), 2.61 (4H, t, J=4.9 Hz, piperazine), 3.54 (4H, t, J=4.9 Hz, piperazine), 4.32 (2H, t, J=7.3 Hz, ArNCH$_2$), 6.95 (1H, ddd, J=9.5, 8.5, 2.3 Hz, Ar), 7.09 (1H, dd, J=10.0, 2.3 Hz, Ar), 7.23 (1H, ddd, J=8.2, 7.2, 1.0 Hz, Ar), 7.34 (1H, ddd, J=8.2, 7.8, 1.0 Hz, Ar), 7.40–7.48 (4H, m, Ar), 7.79 (1H, d, J=8.2 Hz, Ar), 7.88 (1H, d, J=8.2 Hz, Ar), 7.99 (1H, dd, J=8.5, 5.4 Hz, Ar), 8.03 (1H, d, J=8.0 Hz, Ar); MW: 458.65 (C$_{27}$H$_{27}$N$_4$SF); Mass spectrum EIMS, m/z 458.65 (M)$^+$. Hydrochloride: mass spectrum EIMS, m/z 458 (M–HCl)$^+$; Mp: 156°–158° C.

The aforementioned compounds have the structure shown in Table 1.

TABLE 1

| Example | Z | D | E | n | m |
|---|---|---|---|---|---|
| 1 | —N(=O)— | (phenyl) | (vinyl) | 4 | 0 |

TABLE 1-continued

| Example | Z | D | E | n | m |
|---|---|---|---|---|---|
| 2 | −N(CH₃)₂ | benzene-1,2-diyl | 2-methylphenyl | 4 | 0 |
| 3 | −N(CH₃)C(O)− | CH₂−CH₂ | Bond | 4 | 2 |
| 4 | −N(CH₃)C(O)− | benzene-1,2-diyl | 1-methylcyclopentyl | 4 | 0 |
| 5 | −N(CH₃)C(O)− | benzene-1,2-diyl | cis-propenyl | 3 | 0 |
| 6 | −N(CH₃)₂ | benzene-1,2-diyl | 2-methylphenyl | 4 | 2 |

TABLE 2

| Example | Z | D | E | n | m |
|---|---|---|---|---|---|
| 7 | −N(CH₃)C(O)− | benzene-1,2-diyl | 2-methylphenyl | 4 | 2 |
| 8 | −N(CH₃)₂ | benzene-1,2-diyl | N(CH₃)=C(CH₃)Cl | 4 | 0 |
| 9 | −N(CH₃)C(O)− | benzene-1,2-diyl | 2-methylphenyl | 4 | 0 |
| 10 | −O−C(CH₃)=N− | benzene-1,2-diyl | 2-methylphenyl | 4 | 0 |
| 11 | −N(CH₃)C(O)− | 2-(N,N-dimethylamino)phenyl | CH₂−CH₂ | 4 | 0 |

TABLE 3

| Example | Z | D | E | n | m |
|---|---|---|---|---|---|
| 12 | −N(CH₃)₂ | benzene-1,2-diyl | 2-methylphenyl | 3 | 0 |
| 13 | −N(CH₃)C(O)− | cyclohexane-1,2-diyl | −N(CH₃)H | 4 | 0 |
| 14 | −N(CH₃)C(O)− | cyclohexane-1,2-diyl | −N(CH₃)H | 4 | 0 |
| 15 | −N(CH₃)C(O)− | cyclohexane-1,2-diyl | −N(CH₃)H | 2 | 0 |
| 16 | −N(CH₃)C(O)− | cyclohexane-1,2-diyl | −N(CH₃)CH₃ | 4 | 0 |
| 17 | −N(CH₃)C(O)− | cyclohexane-1,2-diyl | −N(CH₃)CH₃ | 3 | 0 |

TABLE 4

| Example | Z | D | E | n | m |
|---|---|---|---|---|---|
| 18 | -N-C(=O)- | cyclohexane | | 4 | 1 |
| 19 | -O-C(=N-)- | -(CH₂)₄-C(=N-)- with E | CH₂-CH-D | 4 | 0 |
| 20 | -N-C(=O)- | benzene | -CH=N- | 4 | 0 |
| 21 | -O-C(=N-)- | benzene | -CH=N- | 4 | 0 |
| 22 | -N-C(=O)- | piperidine (N) | Bond | 4 | 2 |
| 23 | -N-C(=O)- | cyclohexane | Bond | 4 | 2 |

TABLE 5

| Example | Z | D | E | n | m |
|---|---|---|---|---|---|
| 24 | -N-C(=O)- | benzene | CH₂-CH₂ | 4 | 0 |
| 25 | -O-C(=N-)- | CH₃-C(=N-)- | benzene | 4 | 0 |
| 26 | -N(-)- | benzene | benzene-Cl | 4 | 0 |
| 27 | -N(-)- | benzene-Cl | benzene-Cl | 4 | 0 |
| 28 | -N(-)- | benzene | benzene-Cl | 4 | 0 |
| 29 | -N(-)- | benzene | benzene-Cl | 4 | 0 |

TABLE 6

| Example | Z | D | E | n | m |
|---|---|---|---|---|---|
| 30 | -N(-)- | benzene | benzene-F | 4 | 0 |

TABLE 6-continued

| Example | Z | D | E | n | m |
|---|---|---|---|---|---|
| 31 | 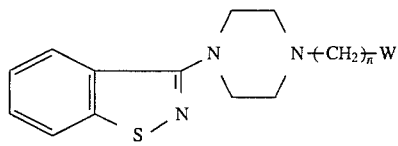 | | | 4 | 0 |

Pharmacological Test

(1) Antipsychotic Activity

Antipsychotic activity was evaluated on the basis of the suppressive activity on the stimulation of hyper locomotion induced by methamphetamine in mice. Male ddY mice having a weight of 25–35 g were divided into groups consisting of 3–6 animals. The mouse was subcutaneously administered with methamphetamine (2 mg/kg) fifteen minutes before the compound of the present invention was intraperitoneally administered. After further fifteen minutes, the animal was then placed in an apparatus to measure the locomotion for thirty minutes. (MUROMACHI KIKAI, ANIMEX AUTO MK-110) The effects of haloperidol and chlorpromazine were also evaluated as controls. The results are shown in Table 7.

TABLE 7

| Anti-methamphetamine effect | |
|---|---|
| Compound | $ED_{50}$ (mg/kg, ip) |
| Example 2 | 1.15 |
| Example 5 | 0.92 |
| Haloperidol | 0.16 |
| Chlorpromazine | 1.05 |

It is obvious from the above that haloperidol and chlorpromazine evaluated as the controls as well as the compounds of Example 2 and 5 have the anti-methamphetamine activity, that is the anti-psychotic activity.

(2) Extrapyramidal side effect

The extrapyramidal activity was evaluated on the basis of the catalepsy provoking effect as a representative pharmacological evaluation method of the extrapyramidal effect. Male ddY mice having a body weight of 25–35 g which were divided into groups consisting of 3–6 animals were subjected to the test. The compound of the present invention was administered intraperitoneally to observe catalepsy after 20, 30 and 40 minutes, respectively. Catalepsy was judged as positive in such cases that a mouse whose front paw was compulsorily hung up on an iron bar having a diameter of 1 mm and horizontally laid at a height of 3 cm remained in such a strained posture for more than 30 seconds. The effects of haloperidol and chlorpromazine as the controls were also evaluated in the similar manner. The results are shown in Table 8.

TABLE 8

| Cataleptogenic activity | |
|---|---|
| Compound | $ED_{50}$ (mg/kg, ip) |
| Example 2 | >100 |
| Example 5 | 83.3 |
| Haloperidol | 1.3 |
| Chlorpromazine | 6.2 |

Both of haloperidol and chlorpromazine have a strong catalepsy provoking effect, that is the extrapyramidal side effect. On the other hand, the compounds obtained in Examples 2 and 5 have a very weak extrapyramidal side effect. The compounds according to the present invention can be considered to be the medicaments having a wide safety zone as an anti-psychotic agent.

(3) Toxicity test

The compound according to the present invention was administered orally or intraperitoneally to male ddY strain mice having a body weight of 25–35 g. At a dose of 100 mg/kg, all of the animals survived for either of the compounds.

What is claimed is:

1. A compound represented by the formula (I)

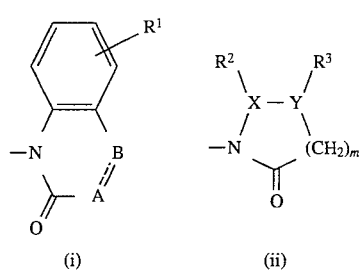

wherein n represents an integer of 2–4, the group W represents any one of the groups represented by the formulae:

wherein m represents an integer of 0–2, the solid line with a dotted line represents a single bond or a double bond, A represents CH$_2$, CH, N or NH, B represents CH$_2$, CH or S, X represents CH, N, S or a bond, Y represents CH or N, Z represents the following groups R$^1$ represents a hydrogen atom, a halogen atom, a lower alkyl group which may be substituted by halogen, an unsubstituted or substituted phenyl group, a hydroxyl group, a nitro group, a lower alkoxy group, an amino group or a cyano group, R$^2$ and R$^3$, which may be the same or different, represent a hydrogen atom, a halogen atom, a lower alkyl which may be substituted with halogen, lower alkoxy or amino group, or a cyano group, provided that when X represents a bond, R$^2$ is not present, or R$^2$ and R$^3$ may represent together a group —(CH$_2$)$_p$—, wherein p represents an integer of 3–5, to form an unsubstituted or substituted saturated ring or heterocyclic saturated ring, or a pharmacologically acceptable salt thereof.

2. A compound represented by the formula (I) according to claim 1, wherein W is the group represented by the formula (vii), wherein Z represents the group (b) and m is 0, or a pharmacologically acceptable salt thereof.

3. A compound represented by the formula (I) according to claim 1, wherein W is the group represented by the formula (iii), or a pharmacologically acceptable salt thereof.

4. A compound according to any one of claims 1–3 selected from the group consisting of
1-[4-[4-(1,2-benzisothiazol-3-yl)-1-piperazinyl]butyl]-2(1H)-quinolinone,
9-[4-[4-(1,2-benzisothiazol-3-yl)-1-piperazinyl]butyl]carbazole,
1-[4-[4-(1,2-benzisothiazol-3-yl)-1-piperazinyl]butyl]-2-piperidone,
1-[4-[4-(1,2-benzisothiazol-3-yl)-1-piperazinyl]butyl]spiro[cyclopentan-1,3'-indol-2-one],
1-[4-[4-(1,2-benzisothiazol-3-yl)-1-piperazinyl]propyl]-2(1H)-quinolinone,
5-[4-[4-(1,2-benzisothiazol-3-yl)-1-piperazinyl]butyl]-10,11-dihydro-5H-dibenz[b,f]azepine,
5-[4-[4-(1,2-benzisothiazol-3-yl)-1-piperazinyl]butyl]-5,6,11,12-tetrahydrodibenz[b,f]azocinn-6-one,
1-[4-[4-(1,2-benzisothiazol-3-yl)-1-piperazinyl]butyl]-3-chloroindazole,
5-[4-[4-(1,2-benzisothiazol-3-yl)-1-piperazinyl]butyl]-6(5H)-phenanthridinone,
6-[4-[4-(1,2-benzisothiazol-3-yl)-1-piperazinyl]butyloxy]phenanthridine,
2-[4-[4-(1,2-benzisothiazol-3-yl)-1-piperazinyl]butyl]-1-phenyl-3-pyrazolidinone,
9-[3-[4-(1,2-benzisothiazol-3-yl)-1-piperazinyl]propyl]carbazole,
1-[4-[4-(1,2-benzisothiazol-3-yl)-1-piperazinyl]butyl]perhydrobenzimidazol-2-one,
1-[3-[4-(1,2-benzisothiazol-3-yl)-1-piperazinyl]propyl]perhydrobenzimidazol-2-one,
1-[2-[4-(1,2-benzisothiazol-3-yl)-1-piperazinyl]ethyl]perhydroimidazol-2-one,
1-[4-[4-(1,2-benzisothiazol-3-yl)-1-piperazinyl]butyl]-3-methylperhydrobenzimidazol-2-one,
1-[3-[4-(1,2-benzisothiazol-3-yl)-1-piperazinyl]propyl]-3-methylperhydrobenzimidazol-2-one,
1-[4-[4-(1,2-benzisothiazol-3-yl)-1-piperazinyl]butyl]perhydroindol-2-one,
1-[4-[4-(1,2-benzisothiazol-3-yl-1-piperazinyl]butyl]perhydropyrido[1,2-a]pyrimidin-2-one,
1-[4-[4-(1,2-benzisothiazol-3-yl)-1-piperazinyl]butyl]perhydroquinolin-2-one,
1-[4-[4-(1,2-benzisothiazol-3-yl)-1-piperazinyl]butyl]-1,2,3,4-tetrahydroquinolin-2-one
4-[1-[4-(1,2-benzisothiazol-3-yl)-1-piperazinyl]butoxy]-2-methylquinazoline,
9-[4-[4-(1,2-benzisothiazol-3-yl)-1-piperazinyl]butyl]-3-chlorocarbazole,
9-[4-[4-(1,2-benzisothiazol-3-yl)-1-piperazinyl]butyl]-3,6-dichlorocarbazole,
9-[4-[4-(1,2-benzisothiazol-3-yl)-1-piperazinyl]butyl]-2-chlorocarbazole,
9-[4-[4-(1,2-benzisothiazol-3-yl)-1-piperazinyl]butyl]-4-chlorocarbazole,
9-[4-[4-(1,2-benzisothiazol-3-yl)-1-piperazinyl]butyl]-3-fluorocarbazole, and
9-[4-[4-(1,2-benzisothiazol-3-yl)-1-piperazinyl]butyl]-2-fluorocarbazole, or
a pharmacologically acceptable salt thereof.

5. An antipsychotic pharmaceutical composition which comprises an effective amount of at least one compound or pharmacologically acceptable salt thereof as defined in claim 1 and a pharmacologically acceptable carrier therefor.

* * * * *